United States Patent
Gil et al.

(10) Patent No.: US 10,913,934 B2
(45) Date of Patent: *Feb. 9, 2021

(54) METHODS AND SYSTEMS FOR RAPID DETECTION OF MICROORGANISMS USING INFECTIOUS AGENTS

(71) Applicant: Laboratory Corporation of American Holdings, Burlington, NC (US)

(72) Inventors: Jose S. Gil, Winnetka, CA (US); Stephen Erickson, White Bear Township, MN (US); Ben Barrett Hopkins, Sherman Oaks, CA (US); Minh Mindy Bao Nguyen, Shoreview, MN (US); Dwight Lyman Anderson, Minneapolis, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/409,258

(22) Filed: Jan. 18, 2017

(65) Prior Publication Data
US 2017/0121688 A1 May 4, 2017

Related U.S. Application Data

(63) Continuation-in-part of application No. 13/773,339, filed on Feb. 21, 2013, now Pat. No. 9,482,668.
(Continued)

(51) Int. Cl.
*C12N 7/00* (2006.01)
*C12Q 1/10* (2006.01)
(Continued)

(52) U.S. Cl.
CPC ............... *C12N 7/00* (2013.01); *C12Q 1/10* (2013.01); *C12Q 1/6804* (2013.01); *C12Q 1/689* (2013.01);
(Continued)

(58) Field of Classification Search
None
See application file for complete search history.

(56) References Cited

U.S. PATENT DOCUMENTS 5,824,468 A 10/1998 Scherer et al.
8,318,474 B1 11/2012 Smolke et al.
(Continued)

FOREIGN PATENT DOCUMENTS

JP 2002-160525 A 6/2002
WO WO 2003/035889 5/2003
(Continued)

OTHER PUBLICATIONS

Tanji et al. *Escherichia coli* detection by GFP-labeled lysozyme-inactivated T4 bacteriophage. J Biotechnol. Oct. 19, 2004;114(1-2):11-20. (Year: 2004).*
(Continued)

*Primary Examiner* — Michelle S Horning
(74) *Attorney, Agent, or Firm* — Kilpatrick Townsend & Stockton LLP

(57) ABSTRACT

Disclosed herein are methods and systems for rapid detection of microorganisms in a sample. A genetically modified bacteriophage is also disclosed which comprises an indicator gene in the late gene region. The specificity of the bacteriophage, such as CBA120, allows detection of a specific microorganism, such as *E. coli* O157:H7, and an indicator signal may be amplified to optimize assay sensitivity.

18 Claims, 17 Drawing Sheets
Specification includes a Sequence Listing.

Related U.S. Application Data

(60) Provisional application No. 62/280,043, filed on Jan. 18, 2016, provisional application No. 62/280,465, filed on Jan. 19, 2016.

(51) Int. Cl.
 *C12Q 1/6804* (2018.01)
 *C12Q 1/689* (2018.01)

(52) U.S. Cl.
 CPC .............. *C12N 2795/00021* (2013.01); *C12N 2795/00052* (2013.01); *C12Q 2600/158* (2013.01)

(56) References Cited

U.S. PATENT DOCUMENTS

| 10,519,483 | B2 | 12/2019 | Anderson et al. |
| 2005/0003346 | A1 | 1/2005 | Voorhees et al. |

FOREIGN PATENT DOCUMENTS

| WO | 2005/001475 | 1/2005 |
| WO | WO 2008/124119 | 10/2008 |
| WO | WO 2013126584 | 8/2013 |
| WO | WO 2015126966 | 8/2015 |

OTHER PUBLICATIONS

Billard and DuBow. Bioluminescence-based assays for detection and characterization of bacteria and chemicals in clinical laboratories. Clin Biochem. Feb. 1998;31(1):1-14. (Year: 1998).*

U.S. Appl. No. 14/625,481, "Non-Final Office Action", dated Jan. 25, 2018, 8 pages.

U.S. Appl. No. 14/625,481, "Non-Final Office Action", dated Apr. 26, 2017, 9 pages.

U.S. Appl. No. 15/263,619, "Non-Final Office Action", dated Mar. 26, 2018, 19 pages.

International Search Report for International Patent Application No. PCT/US2017/013955, dated May 15, 2017.

Elena, C. et al., "Expression of codon optimized genes in microbial systems: current industrial applications and perspectives," Frontiers in Microbiol. 5(21):1-8 (2014).

Kutter, E. et al., "Characterization of a Vil-like Phage Specific to *Escherichia coli* O157:H7," Virology J. 8:430 (2011).

U.S. Appl. No. 15/263,619 , "Final Office Action", dated Feb. 12, 2020, 27 pages.

EP17703002.0 , "Office Action", dated Dec. 18, 2019, 5 pages.

\* cited by examiner

FIG. 10

1mL Concentration

| Tester | Sample | Target Est. Spike | CFU | 5hr RLU | 5hr S/B | 5hr Result | 6hr RLU | 6hr S/B | 6hr Result | 7hr RLU | 7hr S/B | 7hr Result |
|---|---|---|---|---|---|---|---|---|---|---|---|---|
| TD | 1 | 0.2-2 | 1.5 | 81 | 1.6 | Negative | 72 | 1.4 | Negative | 45 | 0.9 | Negative |
| TD | 2 | 3-5 | 7.2 | 1682 | 33.6 | Positive | 20515 | 410.3 | Positive | 109130 | 2182.6 | Positive |
| TD | 3 | 0.2-2 | 1.5 | 125 | 2.5 | Negative | 2836 | 56.7 | Positive | 7959 | 159.2 | Positive |
| TD | 4 | 3-5 | 7.2 | 556 | 11.1 | Positive | 5061 | 101.2 | Positive | 24574 | 491.5 | Positive |
| TD | 5 | 0.2-2 | 1.5 | 93 | 1.9 | Negative | 73 | 1.5 | Negative | 40 | 0.8 | Negative |
| TD | 6 | 0 | 0 | 88 | 1.8 | Negative | 81 | 1.6 | Negative | 47 | 0.9 | Negative |
| TD | 7 | 0 | 0 | 89 | 1.8 | Negative | 78 | 1.6 | Negative | 42 | 0.8 | Negative |
| TD | 8 | 0.2-2 | 1.5 | 76 | 1.5 | Negative | 77 | 1.5 | Negative | 40 | 0.8 | Negative |
| TD | 9 | 0.2-2 | 1.5 | 396 | 7.9 | Positive | 2582 | 51.6 | Positive | 12699 | 254.0 | Positive |
| DH | 10 | 0.2-2 | 1.5 | 82 | 1.6 | Negative | 77 | 1.5 | Negative | 39 | 0.8 | Negative |
| DH | 11 | 0.2-2 | 1.5 | 90 | 1.8 | Negative | 94 | 1.9 | Negative | 58 | 1.2 | Negative |
| DH | 12 | 0.2-2 | 1.5 | 84 | 1.7 | Negative | 81 | 1.6 | Negative | 58 | 1.2 | Negative |
| DH | 13 | 0 | 0 | 84 | 1.7 | Negative | 76 | 1.5 | Negative | 55 | 1.1 | Negative |
| DH | 14 | 0 | 0 | 84 | 1.7 | Negative | 81 | 1.6 | Negative | 54 | 1.1 | Negative |
| DH | 15 | 0.2-2 | 1.5 | 94 | 1.9 | Negative | 86 | 1.7 | Negative | 61 | 1.2 | Negative |
| DH | 16 | 0.2-2 | 1.5 | 81 | 1.6 | Negative | 78 | 1.6 | Negative | 73 | 1.5 | Negative |
| DH | 17 | 0.2-2 | 1.5 | 82 | 1.6 | Negative | 72 | 1.4 | Negative | 50 | 1.0 | Negative |
| DH | 18 | 3-5 | 7.2 | 568 | 11.4 | Positive | 1740 | 34.8 | Positive | 13931 | 278.6 | Positive |
| DH | 19 | 0.2-2 | 1.5 | 88 | 1.8 | Negative | 71 | 1.4 | Negative | 46 | 0.9 | Negative |
| DH | 20 | 0.2-2 | 1.5 | 90 | 1.8 | Negative | 75 | 1.5 | Negative | 53 | 1.1 | Negative |
| HZ | 21 | 3.5 | 7.2 | 176 | 3.5 | Negative | 92 | 1.8 | Negative | 60 | 1.2 | Negative |
| HZ | 22 | 0.2-2 | 1.5 | 183 | 3.7 | Negative | 92 | 1.8 | Negative | 53 | 1.1 | Negative |
| HZ | 23 | 0.2-2 | 1.5 | 166 | 3.3 | Negative | 73 | 1.5 | Negative | 54 | 1.1 | Negative |
| HZ | 24 | 0.2-2 | 1.5 | 180 | 3.6 | Negative | 83 | 1.7 | Negative | 109 | 2.2 | Negative |
| HZ | 25 | 0.2-2 | 1.5 | 179 | 3.6 | Negative | 76 | 1.5 | Negative | 58 | 1.2 | Negative |
| HZ | 26 | 0 | 0 | 172 | 3.4 | Negative | 90 | 1.8 | Negative | 70 | 1.4 | Negative |
| HZ | 27 | 0.2-2 | 1.5 | 149 | 3.0 | Negative | 80 | 1.6 | Negative | 67 | 1.3 | Negative |
| HZ | 28 | 0.2-2 | 1.5 | 166 | 3.3 | Negative | 79 | 1.6 | Negative | 63 | 1.3 | Negative |
| HZ | 29 | 0.2-2 | 1.5 | 156 | 3.1 | Negative | 69 | 1.4 | Negative | 50 | 1.0 | Negative |
| HZ | 30 | 3-5 | 7.2 | 1284 | 25.7 | Positive | 6307 | 126.1 | Positive | 11464 | 229.3 | Positive |

FIG. 11

Summary

| Tester | Sample | Target Est. Spike | CFU | 5hr Result | 6hr Result | 7hr Result | Dynabeads/Chromagar |
|---|---|---|---|---|---|---|---|
| TD | 1 | 0.2-2 | 1.5 | Negative | Negative | Negative | Negative |
| TD | 2 | 3-5 | 7.2 | Positive | Positive | Positive | Positive |
| TD | 3 | 0.2-2 | 1.5 | Negative | Positive | Positive | Positive |
| TD | 4 | 3-5 | 7.2 | Positive | Positive | Positive | Positive |
| TD | 5 | 0.2-2 | 1.5 | Negative | Negative | Negative | Negative |
| TD | 6 | 0 | 0 | Negative | Negative | Negative | Negative |
| TD | 7 | 0 | 0 | Negative | Negative | Negative | Negative |
| TD | 8 | 0.2-2 | 1.5 | Negative | Negative | Negative | Negative |
| TD | 9 | 0.2-2 | 1.5 | Positive | Positive | Positive | Positive |
| TD | 10 | 0.2-2 | 1.5 | Negative | Negative | Negative | Negative |
| DH | 11 | 0.2-2 | 1.5 | Negative | Negative | Negative | Negative |
| DH | 12 | 0.2-2 | 1.5 | Negative | Negative | Negative | Negative |
| DH | 13 | 0 | 0 | Negative | Negative | Negative | Negative |
| DH | 14 | 0 | 0 | Negative | Negative | Negative | Negative |
| DH | 15 | 0.2-2 | 1.5 | Negative | Negative | Negative | Negative |
| DH | 16 | 0.2-2 | 1.5 | Negative | Negative | Negative | Negative |
| DH | 17 | 0.2-2 | 1.5 | Negative | Negative | Negative | Negative |
| DH | 18 | 3-5 | 7.2 | Positive | Positive | Positive | Positive |
| DH | 19 | 0.2-2 | 1.5 | Negative | Negative | Negative | Negative |
| DH | 20 | 0.2-2 | 1.5 | Negative | Negative | Negative | Negative |
| HZ | 21 | 3-5 | 7.2 | Negative | Negative | Negative | Negative |
| HZ | 22 | 0.2-2 | 1.5 | Negative | Negative | Negative | Negative |
| HZ | 23 | 0.2-2 | 1.5 | Negative | Negative | Negative | Negative |
| HZ | 24 | 0.2-2 | 1.5 | Negative | Negative | Negative | Negative |
| HZ | 25 | 0.2-2 | 1.5 | Negative | Negative | Negative | Negative |
| HZ | 26 | 0 | 0 | Negative | Negative | Negative | Negative |
| HZ | 27 | 0.2-2 | 1.5 | Negative | Negative | Negative | Negative |
| HZ | 28 | 0.2-2 | 1.5 | Negative | Negative | Negative | Negative |
| HZ | 29 | 0.2-2 | 1.5 | Negative | Negative | Negative | Negative |
| HZ | 30 | 3-5 | 7.2 | Positive | Positive | Positive | Positive |
| Agreement with Dynabeads/Chromagar | | | | 5hr 29/30 | 6hr 30/30 | 7hr 30/30 | |

FIG. 12

| Tester | Sample | Target Est. Spike | CFU | 5hr 10mL RLU | 5hr S/B | 5hr 10mL Result | Dynabeads/ Chromagar |
|---|---|---|---|---|---|---|---|
| DH | 1 | 0.2-2 | 1.3 | 48 | 1.0 | Negative | Negative |
| DH | 2 | 0.2-2 | 1.3 | 45 | 0.9 | Negative | Negative |
| DH | 3 | 0 | 0 | 48 | 1.0 | Negative | Negative |
| DH | 4 | 0.2-2 | 1.3 | 6726 | 134.5 | Positive | Positive |
| DH | 5 | 0.2-2 | 1.3 | 38 | 0.8 | Negative | Negative |
| DH | 6 | 0.2-2 | 1.3 | 40 | 0.8 | Negative | Negative |
| DH | 7 | 0.2-2 | 1.3 | 40 | 0.8 | Negative | Negative |
| DH | 8 | 0.2-2 | 1.3 | 36 | 0.7 | Negative | Negative |
| DH | 9 | 3-5 | 5.8 | 27106 | 542.1 | Positive | Positive |
| DH | 10 | 0 | 0 | 37 | 0.7 | Negative | Negative |
| DH | 11 | 0.2-2 | 1.3 | 22324 | 446.5 | Positive | Positive |
| DH | 12 | 0.2-2 | 1.3 | 46 | 0.9 | Negative | Negative |
| DH | 13 | 3-5 | 5.8 | 44145 | 882.9 | Positive | Positive |
| DH | 14 | 0.2-2 | 1.3 | 43 | 0.9 | Negative | Negative |
| DH | 15 | 0 | 0 | 39 | 0.8 | Negative | Negative |
| DH | 16 | 0.2-2 | 1.3 | 21480 | 429.6 | Positive | Positive |
| HZ | 17 | 0 | 0 | 49 | 1.0 | Negative | Negative |
| HZ | 18 | 3-5 | 5.8 | 55305 | 1106.1 | Positive | Positive |
| HZ | 19 | 0.2-2 | 1.3 | 66 | 1.3 | Negative | Negative |
| HZ | 20 | 0.2-2 | 1.3 | 48642 | 972.8 | Positive | Positive |
| HZ | 21 | 3-5 | 5.8 | 94223 | 1884.5 | Positive | Positive |
| HZ | 22 | 0.2-2 | 1.3 | 2398 | 48.0 | Positive | Positive |
| HZ | 23 | 3-5 | 5.8 | 13089 | 261.8 | Positive | Positive |
| HZ | 24 | 0.2-2 | 1.3 | 61 | 1.2 | Negative | Negative |
| HZ | 25 | 0.2-2 | 1.3 | 40 | 0.8 | Negative | Negative |
| HZ | 26 | 0.2-2 | 1.3 | 57 | 1.1 | Negative | Negative |
| HZ | 27 | 0.2-2 | 1.3 | 9340 | 186.8 | Positive | Positive |
| HZ | 28 | 0.2-2 | 1.3 | 10864 | 217.3 | Positive | Positive |
| HZ | 29 | 0 | 0 | 48 | 1.0 | Negative | Negative |
| HZ | 30 | 0.2-2 | 1.3 | 54 | 1.1 | Negative | Negative |
| | | | | | | 5hr, 10mL | |
| Agreement with Dynabeads/Chromagar | | | | | | 30/30 | |

FIG. 13

1 mL Concentration

| Tester | Sample | Target Est. Spike | CFU | 7hr RLU | 7hr S/B | 7hr Result | 8hr RLU | 8hr S/B | 8hr Result | 9hr RLU | 9hr S/B | 9hr Result |
|---|---|---|---|---|---|---|---|---|---|---|---|---|
| TD | 1 | 0.2-2 | 0.3 | 153 | 3.1 | Positive | 516 | 10.3 | Positive | 402 | 8.0 | Positive |
| TD | 2 | 0.2-2 | 0.3 | 1200 | 24.0 | Positive | 2654 | 53.1 | Positive | 673 | 13.5 | Positive |
| TD | 3 | 3-5 | 6.1 | 42 | 0.8 | Negative | 43 | 0.9 | Negative | 43 | 0.9 | Negative |
| TD | 4 | 0.2-2 | 0.3 | 45 | 0.9 | Negative | 49 | 1.0 | Negative | 41 | 0.8 | Negative |
| TD | 5 | 0 | 0 | 35 | 0.7 | Negative | 44 | 0.9 | Negative | 37 | 0.7 | Negative |
| TD | 6 | 0.2-2 | 0.3 | 1666 | 33.3 | Positive | 4629 | 92.6 | Positive | 1841 | 36.8 | Positive |
| TD | 7 | 0.2-2 | 0.3 | 37 | 0.7 | Negative | 40 | 0.8 | Negative | 52 | 1.0 | Negative |
| TD | 8 | 0.2-2 | 0.3 | 39 | 0.8 | Negative | 37 | 0.7 | Negative | 39 | 0.8 | Negative |
| TD | 9 | 0 | 0 | 41 | 0.8 | Negative | 41 | 0.8 | Negative | 46 | 0.9 | Negative |
| HZ | 10 | 3-5 | 6.1 | 836 | 16.7 | Positive | 866 | 17.3 | Positive | 634 | 12.7 | Positive |
| HZ | 11 | 0.2-2 | 0.3 | 448 | 9.0 | Positive | 850 | 17.0 | Positive | 2522 | 50.4 | Positive |
| HZ | 12 | 0.2-2 | 0.3 | 42 | 0.8 | Negative | 40 | 0.8 | Negative | 46 | 0.9 | Negative |
| HZ | 13 | 3-5 | 6.1 | 1813 | 36.3 | Positive | 4611 | 92.2 | Positive | 11592 | 231.8 | Positive |
| HZ | 14 | 0.2-2 | 0.3 | 541 | 10.8 | Positive | 526 | 10.5 | Positive | 1276 | 25.5 | Positive |
| HZ | 15 | 0 | 0 | 39 | 0.8 | Negative | 45 | 0.9 | Negative | 46 | 0.9 | Negative |
| HZ | 16 | 0.2-2 | 0.3 | 50 | 1.0 | Negative | 49 | 1.0 | Negative | 49 | 1.0 | Negative |
| HZ | 17 | 0.2-2 | 0.3 | 45 | 0.9 | Negative | 50 | 1.0 | Negative | 52 | 1.0 | Negative |

FIG. 14

| 10 mL Concentration | | Target Est. | | | | | | | | | | |
|---|---|---|---|---|---|---|---|---|---|---|---|---|
| Tester | Sample | Spike | CFU | 7hr RLU | 7hr S/B | 7hr Result | 8hr RLU | 8hr S/B | 8hr Result | 9hr RLU | 9hr S/B | 9hr Result |
| TD | 1 | 0.2-2 | 0.3 | 1162 | 23.2 | Positive | 3190 | 63.8 | Positive | 2250 | 45.0 | Positive |
| TD | 2 | 0.2-2 | 0.3 | 4903 | 98.1 | Positive | 10975 | 219.5 | Positive | 3630 | 72.6 | Positive |
| TD | 3 | 3-5 | 6.1 | 57 | 1.1 | Negative | 54 | 1.1 | Negative | 83 | 1.7 | Negative |
| TD | 4 | 0.2-2 | 0.3 | 47 | 0.9 | Negative | 52 | 1.0 | Negative | 78 | 1.6 | Negative |
| TD | 5 | 0 | 0 | 49 | 1.0 | Negative | 56 | 1.1 | Negative | 102 | 2.0 | Negative |
| TD | 6 | 0.2-2 | 0.3 | 12620 | 252.4 | Positive | 29185 | 583.7 | Positive | 20287 | 405.7 | Positive |
| TD | 7 | 0.2-2 | 0.3 | 48 | 1.0 | Negative | 58 | 1.2 | Negative | 72 | 1.4 | Negative |
| TD | 8 | 0.2-2 | 0.3 | 39 | 0.8 | Negative | 42 | 0.8 | Negative | 62 | 1.2 | Negative |
| TD | 9 | 0 | 0 | 56 | 1.1 | Negative | 65 | 1.3 | Negative | 87 | 1.7 | Negative |
| HZ | 10 | 3-5 | 6.1 | 2592 | 51.8 | Positive | 752 | 15.0 | Positive | 4539 | 90.8 | Positive |
| HZ | 11 | 0.2-2 | 0.3 | 1355 | 27.1 | Positive | 2231 | 44.6 | Positive | 6339 | 126.8 | Positive |
| HZ | 12 | 0.2-2 | 0.3 | 36 | 0.7 | Negative | 46 | 0.9 | Negative | 43 | 0.9 | Negative |
| HZ | 13 | 3-5 | 6.1 | 9058 | 181.2 | Positive | 22867 | 457.3 | Positive | 55912 | 1118.2 | Positive |
| HZ | 14 | 0.2-2 | 0.3 | 1787 | 35.7 | Positive | 2702 | 54.0 | Positive | 4438 | 88.8 | Positive |
| HZ | 15 | 0 | 0 | 53 | 1.1 | Negative | 52 | 1.0 | Negative | 65 | 1.3 | Negative |
| HZ | 16 | 0.2-2 | 0.3 | 52 | 1.0 | Negative | 62 | 1.2 | Negative | 50 | 1.0 | Negative |
| HZ | 17 | 0.2-2 | 0.3 | 50 | 1.0 | Negative | 48 | 1.0 | Negative | 56 | 1.1 | Negative |

FIG. 15

1 mL Concentration Summary

| Tester | Sample | Target Est. Spike | CFU | 7hr Result | 8hr Result | 9hr Result | Dynabeads/ Chromagar |
|---|---|---|---|---|---|---|---|
| TD | 1 | 0.2-2 | 0.3 | Positive | Positive | Positive | Positive |
| TD | 2 | 0.2-2 | 0.3 | Positive | Positive | Positive | Positive |
| TD | 3 | 3-5 | 6.1 | Negative | Negative | Negative | Negative |
| TD | 4 | 0.2-2 | 0.3 | Negative | Negative | Negative | Negative |
| TD | 5 | 0 | 0 | Negative | Negative | Negative | Negative |
| TD | 6 | 0.2-2 | 0.3 | Positive | Positive | Positive | Positive |
| TD | 7 | 0.2-2 | 0.3 | Negative | Negative | Negative | Negative |
| TD | 8 | 0.2-2 | 0.3 | Negative | Negative | Negative | Negative |
| TD | 9 | 0 | 0 | Negative | Negative | Negative | Negative |
| HZ | 10 | 3-5 | 6.1 | Positive | Positive | Positive | Positive |
| HZ | 11 | 0.2-2 | 0.3 | Positive | Positive | Positive | Positive |
| HZ | 12 | 0.2-2 | 0.3 | Negative | Negative | Negative | Negative |
| HZ | 13 | 3-5 | 6.1 | Positive | Positive | Positive | Positive |
| HZ | 14 | 0.2-2 | 0.3 | Positive | Positive | Positive | Positive |
| HZ | 15 | 0 | 0 | Negative | Negative | Negative | Negative |
| HZ | 16 | 0.2-2 | 0.3 | Negative | Negative | Negative | Negative |
| HZ | 17 | 0.2-2 | 0.3 | Negative | Negative | Negative | Negative |
| | | | Agreement with Dynabeads/Chromagar | 7hr 17/17 | 8hr 17/17 | 9hr 17/17 | |

FIG. 16

10 mL Concentration Summary

| Tester | Sample | Target Est. Spike | CFU | 7hr Result | 8hr Result | 9hr Result | Dynabeads/ Chromagar |
|---|---|---|---|---|---|---|---|
| TD | 1 | 0.2-2 | 0.3 | Positive | Positive | Positive | Positive |
| TD | 2 | 0.2-2 | 0.3 | Positive | Positive | Positive | Positive |
| TD | 3 | 3-5 | 6.1 | Negative | Negative | Negative | Negative |
| TD | 4 | 0.2-2 | 0.3 | Negative | Negative | Negative | Negative |
| TD | 5 | 0 | 0 | Negative | Negative | Negative | Negative |
| TD | 6 | 0.2-2 | 0.3 | Positive | Positive | Positive | Positive |
| TD | 7 | 0.2-2 | 0.3 | Negative | Negative | Negative | Negative |
| TD | 8 | 0.2-2 | 0.3 | Negative | Negative | Negative | Negative |
| TD | 9 | 0 | 0 | Negative | Negative | Negative | Negative |
| HZ | 10 | 3-5 | 6.1 | Positive | Positive | Positive | Positive |
| HZ | 11 | 0.2-2 | 0.3 | Positive | Positive | Positive | Positive |
| HZ | 12 | 0.2-2 | 0.3 | Negative | Negative | Negative | Negative |
| HZ | 13 | 3-5 | 6.1 | Positive | Positive | Positive | Positive |
| HZ | 14 | 0.2-2 | 0.3 | Positive | Positive | Positive | Positive |
| HZ | 15 | 0 | 0 | Negative | Negative | Negative | Negative |
| HZ | 16 | 0.2-2 | 0.3 | Negative | Negative | Negative | Negative |
| HZ | 17 | 0.2-2 | 0.3 | Negative | Negative | Negative | Negative |
| | | | | 7hr | 8hr | 9hr | |
| | | | Agreement with Dynabeads/Chromagar | 17/17 | 17/17 | 17/17 | |

FIG. 17

| Number of Cells in Spike | Rep 1 | Rep 2 | Rep 3 | Average RLU/s | SD | %CV | Signal-Background | Signal/Background | Dynabeads/Chromagar |
|---|---|---|---|---|---|---|---|---|---|
| 0 | 9 | 10 | 12 | 10 | 2 | 14.78 | -40 | 0.2 | Negative |
| 1 | 1,591 | 1,050 | 2,074 | 1,572 | 512 | 32.59 | 1,522 | 31.4 | Positive |
| 1 | 434 | 364 | 184 | 327 | 129 | 39.40 | 277 | 6.5 | Positive |
| 0 | 19 | 21 | 23 | 21 | 2 | 9.52 | -29 | 0.4 | Negative |
| 0.7 | 15 | 264 | 35 | 105 | 138 | 132.18 | 55 | 2.1 | Negative |
| 0.7 | 4,314 | 5,409 | 5,663 | 5,129 | 717 | 13.98 | 5,079 | 102.6 | Positive |
| 0 | 18 | 20 | 19 | 19 | 1 | 5.26 | -31 | 0.4 | Negative |
| 0.7 | 22 | 22 | 23 | 22 | 1 | 2.59 | -28 | 0.4 | Negative |
| 7.3 | 17,147 | 17,680 | 18,131 | 17,653 | 493 | 2.79 | 17,603 | 353 | Positive |
| 73 | 87,277 | 86,527 | 90,394 | 88,066 | 2,051 | 2.33 | 88,016 | 1,761 | Positive |

SEQUENCE LISTING

<160> NUMBER OF SEQ ID NOS: 6

<210> SEQ ID NO 1
<211> LENGTH: 500
<212> TYPE: DNA
<213> ORGANISM: genus ViI virus

<400> SEQUENCE: 1

| | | | | | | |
|---|---|---|---|---|---|---|
| ctttcatgct | ggaagttgaa | gcgaacggta | tcggtgttga | cacccgtcgt | ggtaaaggca | 60 |
| accgtgttct | gtgttctccg | aacgtggcat | ccgctctggc | gatgtctggc | atgctggact | 120 |
| atgctccggt | tctgcaggaa | aacactaaac | tggctgttga | cccgactggc | cagaccttcg | 180 |
| ctggtgttct | gtccaacggt | atgcgcgtct | atgttgaccc | gtatgctgta | gcagaatata | 240 |
| tcaccctggc | atacaaaggc | gcaactgcgc | tggatgccgg | tatcttcttc | gcgccgtatg | 300 |
| tgccgctgga | aatgtaccgc | acccagggtg | aaaccacctt | cgctccgcgt | atggcgttca | 360 |
| aaacccgtta | cggcatctgt | gctaacccgt | tcgtacagat | tccggctaac | caagacccgc | 420 |
| aggtttacgt | gactgctgac | ggtattgctc | aagacagcaa | cccgtatttc | gcaaaggtc | 480 |
| tgatcaaatc | tctgttctaa | | | | | 500 |

<210> SEQ ID NO 2
<211> LENGTH: 11
<212> TYPE: DNA
<213> ORGANISM: Artificial Sequence
<220> FEATURE:
<223> OTHER INFORMATION: synthetic consensus binding sequence

<400> SEQUENCE: 2

| | |
|---|---|
| ctaaataccc c | 11 |

<210> SEQ ID NO 3
<211> LENGTH: 45
<212> TYPE: DNA
<213> ORGANISM: Artificial Sequence
<220> FEATURE:
<223> OTHER INFORMATION: synthetic bacteriophage nucleotide sequence

<400> SEQUENCE: 3

| | | | | |
|---|---|---|---|---|
| acgcgtctaa | ataccccaaa | tactagtaga | taaggaggtt | ttcga | 45 |

<210> SEQ ID NO 4
<211> LENGTH: 600
<212> TYPE: DNA
<213> ORGANISM: Artificial Sequence
<220> FEATURE:
<223> OTHER INFORMATION: synethetic bacteriophage nucleotide sequence

<400> SEQUENCE: 4

| | | | | | | |
|---|---|---|---|---|---|---|
| atgaatagct | ttagcaccag | cgcctttggc | cctgttgcct | ttagcctggg | cctgctgctg | 60 |
| gttctgccgg | cagcatttcc | ggccccggtg | ttcaccctgg | aagattttgt | gggcgattgg | 120 |
| cgccagaccg | ccggttataa | cctggatcag | gtgctggaac | agggtggtgt | gagcagcctg | 180 |
| tttcagaatc | tgggcgtgag | cgtgacccCg | attcagcgca | ttgtgctgag | cggcgagaac | 240 |
| ggcctgaaaa | ttgatattca | tgttattatt | ccgtatgagg | gtctgagcgg | cgatcagatg | 300 |
| ggccagattg | aaaaaatctt | taaggtggtg | tatccggtgg | acgaccatca | tttcaaggtg | 360 |
| atcctgcatt | acggcacact | ggtgattgac | ggcgttaccc | gaacatgat | cgactatttc | 420 |
| ggccgccccgt | atgaaggtat | cgccgtgttc | gacggcaaga | aaattaccgt | gaccggtacc | 480 |
| ctgtggaacg | gcaacaagat | cattgacgag | cgcctgatta | cccggatgg | tagcctgctg | 540 |

```
tttcgcgtga ccattaatgg cgtgaccggc tggcgtctgt gtgaacgcat cctggcctaa        600

<210> SEQ ID NO 5
<211> LENGTH: 298
<212> TYPE: DNA
<213> ORGANISM: Artificial Sequence
<220> FEATURE:
<223> OTHER INFORMATION: synethetic bacteriophage nucleotide sequence

<400> SEQUENCE: 5
gcgacaggtt ttgataacaa accccgcttc ggcggggttt ttctttatag ggatatgtaa         60
gataataaag cctcatttat caaaggaggt taaaatgtct catcaattat ctggcggtgc        120
agtcgatact ctattcgttc ttttctggtt tggacctcgt gaagctgggg aaatacctgc        180
taaatctgga gaagccgaat tggcctccct ggggttttgt aaacgagttg atgttaaaaa        240
cgtaccaaaa ggtcgagata cacatctgtg tgtactcacc gaggaaggtt acaaatac         298

<210> SEQ ID NO 6
<211> LENGTH: 45
<212> TYPE: DNA
<213> ORGANISM: Artificial Sequence
<220> FEATURE:
<223> OTHER INFORMATION: synethetic bacteriophage nucleotide sequence

<400> SEQUENCE: 6
taatttgata acaaaccccg cttcggcggg gtttttcttt atagg                         45
```

METHODS AND SYSTEMS FOR RAPID DETECTION OF MICROORGANISMS USING INFECTIOUS AGENTS

RELATED APPLICATIONS

The present application claims priority to U.S. Provisional Patent Application No. 62/280,043, filed Jan. 18, 2016 and U.S. Provisional Patent Application No. 62/280,465, filed Jan. 19, 2016. The disclosures of U.S. Provisional Patent Application Nos. 62/280,043 and 62/280,465 are hereby incorporated by reference in their entirety herein. This application is a Continuation-in-Part of U.S. application Ser. No. 13/773,339, filed Feb. 21, 2013 and is related to U.S. application Ser. No. 14/625,481, filed Feb. 18, 2015; and U.S. application Ser. No. 15/263,619, filed Sep. 13, 2016. The disclosures of U.S. application Ser. Nos. 13/773,339, 14/625,481, and 15/263,619 are hereby incorporated by reference in their entirety herein.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1035090_ST25.txt, created on Jan. 17, 2017, and having a size of 7 kilobytes and is filed concurrently with the specification. The sequence listing contained in this ASCII formatted document is part of the specification and is herein incorporated by reference in its entirety.

FIELD OF THE INVENTION

This invention relates to methods and systems for the detection of microorganisms using infectious agents.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Also, detection of microorganisms is a high priority for the Food and Drug Administration (FDA) and Centers for Disease Control (CDC) given outbreaks of life-threatening or fatal illness caused by ingestion of food contaminated with certain microorganisms, e.g., *Escherichia coli* or *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an overnight enrichment step in order to obtain adequate sensitivity. Polymerase chain reaction (PCR) tests also include an amplification step and therefore are capable of both very high sensitivity and selectivity; however, the sample size that can be economically subjected to PCR testing is limited. With dilute bacterial suspensions, most small subsamples will be free of cells and therefore purification and/or lengthy enrichment steps are still required.

The time required for traditional biological enrichment is dictated by the growth rate of the target bacterial population of the sample, by the effect of the sample matrix, and by the required sensitivity. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water (or other product) may have already made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple and sensitive detection and identification of microorganisms, such as bacteria and other potentially pathogenic microorganisms.

SUMMARY

Embodiments of the invention comprise compositions, methods, systems and kits for the detection of microorganisms. The invention may be embodied in a variety of ways.

In some aspects, the invention comprises a recombinant bacteriophage comprising an indicator gene inserted into a late gene region of a bacteriophage genome. In some embodiments the recombinant bacteriophage is a genetically modified CBA120 genome. In some embodiments the recombinant bacteriophage is a genetically modified T4-like or ViI-like bacteriophage genome. In some embodiments the recombinant bacteriophage specifically infects *E. coli* O157:H7. In an embodiment, the recombinant bacteriophage can distinguish *E. coli* O157:H7 in the presence of more than 100 other types of bacteria.

In some embodiments of recombinant indicator bacteriophage, the indicator gene can be codon-optimized and can encode a soluble protein product that generates an intrinsic signal or a soluble enzyme that generates signal upon reaction with substrate. Some recombinant bacteriophage further comprise an untranslated region upstream of a codon-optimized indicator gene, wherein the untranslated region includes a bacteriophage late gene promoter and a ribosomal entry site. In some embodiments, the indicator gene is a luciferase gene. The luciferase gene can be a naturally occurring gene, such as *Oplophorus* luciferase, Firefly luciferase, Lucia luciferase, or *Renilla* luciferase, or it can be a genetically engineered gene.

Also disclosed herein are methods for preparing a recombinant indicator bacteriophage. Some embodiments include selecting a wild-type bacteriophage that specifically infects a target pathogenic bacterium; preparing a homologous recombination plasmid/vector comprising an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage. In some embodiments the selected wild-type bacteriophage is CBA120. In some embodiments the selected wild-type bacteriophage is T4-like or ViI-like.

In some embodiments, preparing a homologous recombination plasmid/vector includes determining the natural nucleotide sequence in the late region of the genome of the selected bacteriophage; annotating the genome and identifying the major capsid protein gene of the selected bacteriophage; designing a sequence for homologous recombination downstream of the major capsid protein gene, wherein the sequence comprises a codon-optimized indicator gene; and incorporating the sequence designed for homologous recombination into a plasmid/vector. The step of designing a sequence can include inserting an untranslated region, including a phage late gene promoter and ribosomal entry site, upstream of the codon-optimized indicator gene. Thus in some methods the homologous recombination plasmid comprises an untranslated region including a bacteriophage late gene promoter and a ribosomal entry site upstream of the codon-optimized indicator gene.

Some embodiments of the invention are compositions that include a recombinant indicator bacteriophage as described herein. For example, compositions can include one or more wild-type or genetically modified infectious agents (e.g., bacteriophages) and one or more indicator genes. In some embodiments, compositions can include cocktails of different indicator phages that may encode and express the same or different indicator proteins.

In some embodiments, the invention comprises a method for detecting a microorganism of interest in a sample comprising the steps of incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product, and detecting the indicator protein product, wherein positive detection of the indicator protein product indicates that the microorganism of interest is present in the sample.

In some embodiments of methods for preparing recombinant indicator bacteriophage, the wild-type bacteriophage is CBA120 and the target pathogenic bacterium is $E.\ coli$ O157:H7. In some embodiments, isolating a particular clone of recombinant bacteriophage comprises a limiting dilution assay for isolating a clone that demonstrates expression of the indicator gene.

Other aspects of the invention include methods for detecting bacteria, such as $E.\ coli$ O157:H7, in a sample, including steps of incubating the sample with a recombinant bacteriophage derived from CBA120 and detecting an indicator protein product produced by the recombinant bacteriophage, wherein positive detection of the indicator protein product indicates that $E.\ coli$ O157:H7 is present in the sample. The sample can be a food, environmental, water, commercial, or clinical sample. In some embodiments, the sample comprises beef or vegetables.

In some embodiments of methods for detecting bacteria, the sample is first incubated in conditions favoring growth for an enrichment period of 9 hours or less, 8 hours or less, 7 hours or less, 6 hours or less, 5 hours or less, 4 hours or less, 3 hours or less, or 2 hours or less. In some embodiments, the total time to results is less than 12 hours, less than 11 hours, less than 10 hours, less than 9 hours, less than 8 hours, less than 7 hours, or less than 6 hours. In some embodiments, the ratio of signal to background generated by detecting the indicator is at least 2.0 or at least 2.5. In some embodiments, the method detects as few as 1, 2, 3, 4, 5, 6, 7, 8, 9, 10, 15, 20, 30, 40, 50, 60, 70, 80, 90, or 100 of the specific bacteria in a sample of a standard size for the food safety industry.

Additional embodiments include systems and kits for detecting $E.\ coli$ O157:H7, wherein the systems or kits include a recombinant bacteriophage derived from CBA120. Some embodiments further include a substrate for reacting with an indicator to detect the soluble protein product expressed by the recombinant bacteriophage. These systems or kits can include features described for the bacteriophage, compositions, and methods of the invention. In still other embodiments, the invention comprises non-transient computer readable media for use with methods or systems according to the invention.

BRIEF DESCRIPTION OF THE FIGURES

The present invention may be better understood by referring to the following non-limiting figures.

FIG. 10 shows Relative Light Units (RLU) and signal to background ratios for detection of $E.\ coli$ O157:H7 in a 1 mL concentration sample from 25 g ground beef when the assay is conducted after 5, 6, and 7 hours of enrichment.

FIG. 11 summarizes detection of $E.\ coli$ O157:H7 in a 1 mL concentration sample from 25 g ground beef as shown in FIG. 10 with confirmation of the results using a secondary method.

FIG. 12 shows RLU and signal to background ratios for detection of $E.\ coli$ O157:H7 in a 10 mL concentration sample from 25 g ground beef when the assay is conducted after 5 hours of enrichment with confirmation of the results using a secondary method.

FIG. 13 shows RLU and signal to background ratios for detection of *E. coli* O157:H7 in 1 mL concentration samples from 125 g beef trim when the assay is conducted after 7, 8, and 9 hours of enrichment.

FIG. 14 shows RLU and signal to background ratios for detection of *E. coli* O157:H7 in 10 mL concentration samples from 125 g beef trim when the assay is conducted after 7, 8, and 9 hours of enrichment.

FIG. 15 summarizes detection of *E. coli* O157:H7 in 1 mL concentration samples from 125 g beef trim as shown in FIG. 13 with confirmation of the results using a secondary method.

FIG. 16 summarizes detection of *E. coli* O157:H7 in 10 mL concentration samples from 125 g beef trim as shown in FIG. 14 with confirmation of the results using a secondary method.

FIG. 17 shows RLU and signal to background ratios for detection of *E. coli* O157:H7 in 100 mL spinach wash filtered and subjected to a filter assay format with confirmation of the results using a secondary method.

DETAILED DESCRIPTION OF THE INVENTION

Figure 1:
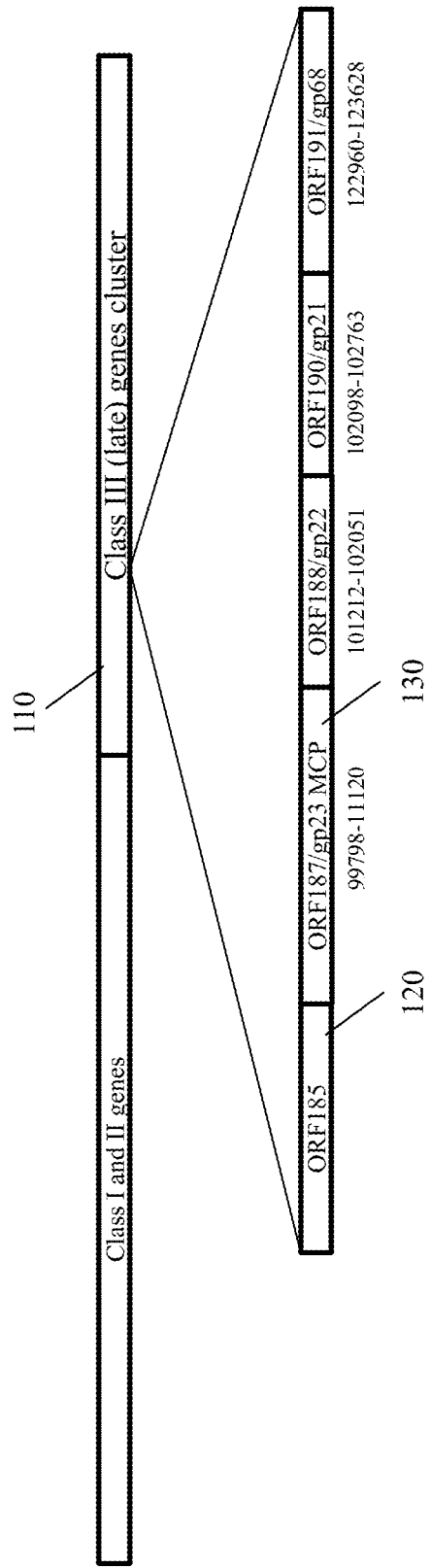
FIG. 1 shows a portion of the genome of the wild-type CBA120 bacteriophage and the annotated late gene region in particular.

Disclosed herein are compositions, methods and systems that demonstrate surprising sensitivity for detection of a microorganism of interest in test samples (e.g., biological, food, water, and clinical samples). Detection can be achieved in a shorter timeframe than was previously thought possible using genetically modified infectious agents in assays performed without culturing for enrichment, or in some embodiments with minimal incubation times during which microorganisms could potentially multiply. Also surprising is the success of using a potentially high multiplicity of infection (MOI), or high concentrations of plaque forming units (PFU), for incubation with a test sample. Such high phage concentrations (PFU/mL) were previously purported to be detrimental in bacterium detection assays, as they were purported to cause "lysis from without." However, a high concentration of phage can facilitate finding, binding, and infecting a low number of target cells.

The compositions, methods, systems and kits of the invention may comprise infectious agents for use in detection of such microorganisms. In certain embodiments, the invention may comprise a composition comprising a recombinant bacteriophage having an indicator gene inserted into a late gene region of the bacteriophage. In certain embodiments, expression of the indicator gene during bacteriophage replication following infection of a host bacterium results in production of a soluble indicator protein product. In certain embodiments, the indicator gene may be inserted into a late gene (i.e., class III) region of the bacteriophage. The bacteriophage can be derived from T7, T4, T4-like, ViI, ViI-like (or Vi1 virus, per GenBank/NCBI), CBA120, or another wild-type or engineered bacteriophage.

In some aspects, the invention comprises a method for detecting a microorganism of interest. The method may use an infectious agent for detection of the microorganism of interest. For example, in certain embodiments, the microorganism of interest is a bacterium and the infectious agent is a bacteriophage. Thus, in certain embodiments, the method may comprise detection of a bacterium of interest in a sample by incubating the sample with a recombinant bacteriophage that infects the bacterium of interest. In certain embodiments, the recombinant bacteriophage comprises an indicator gene. The indicator gene may, in certain embodiments, be inserted into a late gene region of the bacteriophage such that expression of the indicator gene during bacteriophage replication following infection of host bacteria results in production of an indicator protein product. The method may comprise detecting the indicator protein product, wherein positive detection of the indicator protein product indicates that the bacterium of interest is present in the sample. In some embodiment the indicator protein is soluble.

In certain embodiments, the invention may comprise a system. The system may contain at least some of the compositions of the invention. Also, the system may comprise at least some of the components for performing the method. In certain embodiments, the system is formulated as a kit. Thus, in certain embodiments, the invention may comprise a system for rapid detection of a microorganism of interest in a sample, comprising: a component for incubating the sample with an infectious agent specific for the microorganism of interest, wherein the infectious agent comprises an indicator moiety; and a component for detecting the indicator moiety. In yet other embodiments, the invention comprises software for use with the methods or systems.

Thus, some embodiments of the present invention solve a need by using bacteriophage-based methods for amplifying a detectable signal indicating the presence of bacteria. In certain embodiments as little as a single bacterium is detected. The principles applied herein can be applied to the detection of a variety of microorganisms. Because of numerous binding sites for an infectious agent on the surface of a microorganism, the capacity to produce one hundred or more agent progeny during infection, and the potential for high level expression of an encoded indicator moiety, the infectious agent or an indicator moiety can be more readily detectable than the microorganism itself. In this way, embodiments of the present invention can achieve tremendous signal amplification from even a single infected cell.

Aspects of the present invention utilize the high specificity of binding agents that can bind to particular microorganisms, such as the binding component of infectious agents, as a means to detect and/or quantify the specific microorganism in a sample. In some embodiments, the present invention utilizes the high specificity of infectious agents such as bacteriophage.

In some embodiments, detection is achieved through an indicator moiety associated with the binding agent specific for the microorganism of interest. For example, an infectious agent may comprise an indicator moiety, such as a gene encoding a soluble indicator. In some embodiments the indicator may be encoded by the infectious agent, such as a bacteriophage, and the bacteriophage is designated an indicator phage.

Some embodiments of the invention disclosed and described herein utilize the discovery that a single microorganism is capable of binding specific recognition agents, such as phage. Following infection and replication of the phage, progeny phage may be detected via an indicator moiety expressed during phage replication. This principle allows amplification of indicator signal from one or a few cells based on specific recognition of microorganism surface receptors. For example, by exposing even a single cell of a bacterium to a plurality of phage, thereafter allowing amplification of the phage and high-level expression of an encoded indicator gene product during replication, the indicator signal is amplified such that the single bacterium is detectable.

Embodiments of the methods and systems of the invention can be applied to detection and quantification of a variety of microorganisms (e.g., bacteria, fungi, yeast) in a variety of circumstances, including but not limited to detection of pathogens from food, water, clinical and commercial samples. The methods of the present invention provide high detection sensitivity and specificity rapidly and without the need for traditional biological enrichment (e.g., culturing for enrichment), which is a surprising aspect as all available methods require culturing. In some embodiments detection is possible within a single replication cycle of the bacteriophage, which is unexpected.

DEFINITIONS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate or lateral flow strip).

The term "binding agent" refers to a molecule that can specifically and selectively bind to a second (i.e., different) molecule of interest. The interaction may be non-covalent, for example, as a result of hydrogen bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator" or "indicator moiety" refers to a molecule that can be measured in a quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, *mycoplasma*, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III,) are transcribed in phage T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for very short periods of time may be employed in some embodiments of methods described herein, but is not necessary and is for a much shorter period of time than traditional culturing for enrichment, if it is used at all.

As used herein "recombinant" refers to genetic (i.e., nucleic acid) modifications as usually performed in a laboratory to bring together genetic material that would not otherwise be found. This term is used interchangeably with the term "modified" herein.

As used herein "RLU" refers to relative light units as measured by a luminometer (e.g., GLOMAX® 96) or similar instrument that detects light. For example, the detection of the reaction between luciferase and appropriate substrate (e.g., NANOLUC® with NANO-GLO®) is often reported in RLU detected.

As used herein "time to results" refers to the total amount of time from beginning of sample preparation to the collection of data. Time to results does not include any confirmatory testing time.

Samples

Each of the embodiments of the methods and systems of the invention can allow for the rapid detection and quantification of microbes in a sample. For example, methods according to the present invention can be performed in a shortened time period with superior results.

Microbes detected by the methods and systems of the present invention include pathogens that are of natural, commercial, medical or veterinary concern. Such pathogens include Gram-negative bacteria, Gram-positive bacteria, mycoplasmas and viruses. Any microbe for which an infectious agent that is specific for the particular microbe has been identified can be detected by the methods of the present invention. Those skilled in the art will appreciate that there is no limit to the application of the present methods other than the availability of the necessary specific infectious agent/microbe pairs.

Bacterial cells detectable by the present invention include, but are not limited to, bacterial cells that are food or water borne pathogens. Bacterial cells detectable by the present invention include, but are not limited to, all species of *Salmonella*, all strains of *Escherichia coli*, including, but not limited to *E. coli* O157:H7, all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis, Camplyobacter jejuni, Chlamydia pneumoniae, Clostridium perfringens, Enterobacter* spp., *Klebsiella pneumoniae, Mycoplasma pneumoniae, Salmonella typhi, Shigella sonnei, Staphylococcus aureus*, and *Streptococcus* spp.

The sample may be an environmental or food or water sample. Some embodiments may include medical or veterinary samples. Samples may be liquid, solid, or semi-solid. Samples may be swabs of solid surfaces. Samples may include environmental materials, such as the water samples, or the filters from air samples or aerosol samples from cyclone collectors. Samples may be of meat, poultry, processed foods, milk, cheese, or other dairy products. Medical or veterinary samples include, but are not limited to, blood, sputum, cerebrospinal fluid, and fecal samples and different types of swabs.

In some embodiments, samples may be used directly in the detection methods of the present invention, without preparation, concentration, or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to $Na^+$, $Mg^{2+}$, and $K^+$. Preferably a sample is maintained at a temperature that maintains the viability of any pathogen cells contained within the sample.

Preferably throughout detection assays, the sample is maintained at a temperature that maintains the viability of any pathogen cell present in the sample. During steps in which bacteriophages are attaching to bacterial cells, it is preferable to maintain the sample at a temperature that facilitates bacteriophage attachment. During steps in which bacteriophages are replicating within an infected bacterial cell or lysing such an infected cell, it is preferable to maintain the sample at a temperature that promotes bacteriophage replication and lysis of the host. Such temperatures are at least about 25 degrees Celsius (C), more preferably no greater than about 45 degrees C., most preferably about 37 degrees C. It is also preferred that the samples be subjected to gentle mixing or shaking during bacteriophage attachment, replication and cell lysis.

Assays may include various appropriate control samples. For example, control samples containing no bacteriophages or control samples containing bacteriophages without bacteria may be assayed as controls for background signal levels.

Indicator Bacteriophage

As described in more detail herein, the compositions, methods, systems and kits of the invention may comprise infectious agents for use in detection of pathogenic microorganisms. In certain embodiments, the invention comprises a recombinant indicator bacteriophage, wherein the bacteriophage genome is genetically modified to include an indicator or reporter gene. In some embodiments, the invention may include a composition comprising a recombinant bacteriophage having an indicator gene incorporated into the genome of the bacteriophage.

A recombinant indicator bacteriophage can include a reporter or indicator gene. In certain embodiments of the infectious agent, the indicator gene does not encode a fusion protein. For example, in certain embodiments, expression of the indicator gene during bacteriophage replication following infection of a host bacterium results in a soluble indicator protein product. In certain embodiments, the indicator gene may be inserted into a late gene region of the bacteriophage. Late genes are generally expressed at higher levels than other phage genes, as they code for structural proteins. The late gene region may be a class III gene region and may include a gene for a major capsid protein.

Some embodiments include designing (and optionally preparing) a sequence for homologous recombination downstream of the major capsid protein gene. In some embodiments, the sequence comprises a codon-optimized reporter gene preceded by an untranslated region. The untranslated region may include a phage late gene promoter and ribosomal entry site.

In some embodiments, an indicator bacteriophage is derived from T7, T4 or another similar phage. An indicator bacteriophage may also be derived from T4-like, T7-like, ViI, ViI-like, CBA120, or another bacteriophage having a genome with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to T7, T7-like, T4, T4-like, CBA120, ViI, or ViI-like (or ViI virus-like, per GenBank/NCBI) bacteriophages. In some embodiments, the indicator phage is derived from a bacteriophage that is highly specific for a particular pathogenic microorganism. The genetic modifications may avoid deletions of wild-type genes and thus the modified phage may remain more similar to the wild-type infectious agent than many commercially available phage. Environmentally derived bacteriophage may be more specific for bacteria that are found in the environment and as such, genetically distinct from phage available commercially.

Moreover, phage genes thought to be nonessential may have unrecognized function. For example, an apparently nonessential gene may have an important function in elevating burst size such as subtle cutting, fitting, or trimming functions in assembly. Therefore, deleting genes to insert an indicator may be detrimental. Most phages can package a DNA that is a few percent larger than their natural genome. With this consideration, a smaller indicator gene may be a more appropriate choice for modifying a bacteriophage, especially one with a smaller genome. OpLuc and NANOLUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp, and the genome of CBA120 is about 157 kbp. Moreover, the reporter gene should not be expressed endogenously by the bacteria (i.e., is not part of the bacterial genome), should generate a high signal to background ratio, and should be readily detectable in a timely manner. Promega's NANOLUC® is a modified *Oplophorus gracilirostris* (deep sea shrimp) luciferase. In some embodiments, NANOLUC® combined with Promega's NANO-GLO®, an imidazopyrazinone substrate (furimazine), can provide a robust signal with low background.

In some indicator phage embodiments, the indicator gene can be inserted into an untranslated region to avoid disruption of functional genes, leaving wild-type phage genes intact, which may lead to greater fitness when infecting non-laboratory strains of bacteria. Additionally, including stop codons in all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various types of luciferase may be used. In alternate embodiments, and as described in more detail herein, the luciferase is one of *Oplophorus* luciferase, Firefly luciferase, Lucia luciferase, *Renilla* luciferase, or an engineered luciferase. In some embodiments, the luciferase gene is derived from *Oplophorus*. In some embodiments, the indicator gene is a genetically modified luciferase gene, such as NANOLUC®.

Thus, in some embodiments, the present invention comprises a genetically modified bacteriophage comprising a non-bacteriophage indicator gene in the late (class III) gene region. In some embodiments, the non-native indicator gene is under the control of a late promoter. Using a viral late gene promoter insures the reporter gene (e.g., luciferase) is not only expressed at high levels, like viral capsid proteins, but also does not shut down like endogenous bacterial genes or even early viral genes.

In some embodiments, the late promoter is a T4-, T7-, or ViI-like promoter, or another phage promoter similar to that found in the selected wild-type phage, i.e., without genetic modification. The late gene region may be a class III gene region, and the bacteriophage may be derived from T7, T4, T4-like, ViI, ViI-like, CBA120, or another natural bacteriophage having a genome with at least 70, 75, 80, 85, 90 or 95% homology to T7, T4, T4-like, ViI, ViI-like, or CBA120 phage.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. In some embodiments, the non-native indicator gene is not part of a fusion protein. That is, in some embodiments, a genetic modification may be configured such that the indicator protein product does not comprise polypeptides of the wild-type bacteriophage. In some embodiments, the indicator protein product is soluble. In some embodiments, the invention comprises a method for detecting a bacterium of interest comprising the step of incubating a test sample with such a recombinant bacteriophage.

In some embodiments, expression of the indicator gene in progeny bacteriophage following infection of host bacteria results in a free, soluble protein product. In some embodiments, the non-native indicator gene is not contiguous with a gene encoding a structural phage protein and therefore does not yield a fusion protein. Unlike systems that employ a fusion of a detection moiety to the capsid protein (i.e., a fusion protein), some embodiments of the present invention express a soluble luciferase. This may greatly increase the sensitivity of the assay (down to a single bacterium), and simplifies the assay, allowing the assay to be completed in less than an hour for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate.

Moreover, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the detection moiety (e.g., luciferase) than can fit on the bacteriophage. Additionally, large fusion proteins, such as a capsid-luciferase fusion, may inhibit assembly of the bacteriophage particle, thus yielding fewer bacteriophage progeny. Thus a soluble, non-fusion indicator gene product may be preferable.

In some embodiments, the indicator phage encodes a reporter, such as a detectable enzyme. The indicator gene product may generate light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, *Oplophorus* luciferase is the indicator moiety. In some embodiments, NANOLUC® is the indicator moiety. Other engineered luciferases or other enzymes that generate detectable signals may also be appropriate indicator moieties.

In some embodiments, the use of a soluble detection moiety eliminates the need to remove contaminating parental phage from the lysate of the infected sample cells. With a fusion protein system, any bacteriophage used to infect sample cells would have the detection moiety attached, and would be indistinguishable from the daughter bacteriophage also containing the detection moiety. As detection of sample bacteria relies on the detection of a newly created (de novo synthesized) detection moiety, using fusion constructs requires additional steps to separate old (parental) moieties from newly created (daughter bacteriophage) moieties. This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by streptavidin-coated sepharose beads). However, even with all these attempts at removal, parental phage can remain when a high concentration of parental phage is used to assure infection of a low number of sample cells, creating background signal that may obscure detection of signal from infected cell progeny phage.

By contrast, with the soluble detection moiety expressed in some embodiments of the present invention, purification of the parental phage from the final lysate is unnecessary, as the parental phage do not have any detection moiety attached. Thus any detection moiety present after infection must have been created de novo, indicating the presence of an infected bacterium or bacteria. To take advantage of this benefit, the production and preparation of parental phage may include purification of the phage from any free detection moiety produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). Cesium chloride isopycnic ultracentrifugation can be employed as part of the preparation of recombinant phage of the invention, to separate parental phage particles from contaminating luciferase protein produced upon propagation of the phage in the bacterial host. In this way, the parental recombinant bacteriophage of the invention is substantially free of any luciferase generated during production in the bacteria. Removal of residual luciferase present in the phage stock can substantially reduce background signal observed when the recombinant bacteriophage are incubated with a test sample.

In some embodiments of modified bacteriophage, the late promoter (class III promoter, e.g., from T7, T4, or ViI) has high affinity for RNA polymerase of the same bacteriophage that transcribes genes for structural proteins assembled into the bacteriophage particle. These proteins are the most abundant proteins made by the phage, as each bacteriophage particle comprises dozens or hundreds of copies of these molecules. The use of a viral late promoter can ensure optimally high level of expression of the luciferase detection moiety. The use of a late viral promoter derived from, specific to, or active under the original wild-type bacteriophage the indicator phage is derived from (e.g., a T4, T7, or ViI late promoter with a T4-, T7-, or ViI-based system) can further ensure optimal expression of the detection moiety. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator moiety, using a placement in the genome that does not limit expression to the number of subunits of a phage structural component.

Compositions of the invention may comprise one or more wild-type or genetically modified infectious agents (e.g., bacteriophages) and one or more indicator genes. In some embodiments, compositions can include cocktails of different indicator phages that may encode and express the same or different indicator proteins.

Methods of Preparing Indicator Bacteriophage

Embodiments of methods for making indicator bacteriophage begin with selection of a wild-type bacteriophage for genetic modification. Some bacteriophage are highly specific for a target bacterium. This presents an opportunity for highly specific detection.

Thus, the methods of the present invention utilizes the high specificity of binding agents, associated with infectious agents, that recognize and bind to a particular microorganism of interest as a means to amplify a signal and thereby detect low levels of a microorganism (e.g., a single microorganism) present in a sample. For example, infectious agents (e.g., bacteriophage) specifically recognize surface receptors of particular microorganisms and thus specifically infect those microorganisms. As such, these infectious agents may be appropriate binding agents for targeting a microorganism of interest.

A variety of infectious agents may be used. In alternate embodiments, bacteriophages, phages, mycobacteriophages (such as for TB and paraTB), mycophages (such as for fungi), *mycoplasma* phages, and any other virus that can invade living bacteria, fungi, *mycoplasma*, protozoa, yeasts, and other microscopic living organisms can be employed to target a microorganism of interest. For example, in an embodiment, where the microorganism of interest is a bacterium, the infectious agent may comprise a bacteriophage. For example, well-studied phages of *E. coli* include T1, T2, T3, T4, T5, T7, and lambda; other *E. coli* phages available in the ATCC collection, for example, include phiX174, S13, Ox6, MS2, phiV1, fd, PR772, and ZIK1. As discussed herein, the bacteriophage may replicate inside of the bacteria to generate hundreds of progeny phage. Detection of the product of an indicator gene inserted into the bacteriophage genome can be used as a measure of the bacteria in the sample.

Some embodiments of the invention utilize the specificity of binding and high-level genetic expression capacity of recombinant bacteriophage for rapid and sensitive targeting to infect and facilitate detection of a bacterium of interest. In some embodiments, CBA120 bacteriophage is genetically modified to include a reporter gene. In some embodiments the late gene region of a bacteriophage is genetically modified to include a reporter gene. In some embodiments, a reporter gene is positioned downstream of the major capsid gene. In other embodiments, a reporter gene is positioned upstream of the major capsid gene.

Some embodiments of methods for preparing a recombinant indicator bacteriophage include selecting a wild-type bacteriophage that specifically infects a target pathogenic bacterium; preparing a homologous recombination plasmid/vector that comprises an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage.

Various methods for designing and preparing a homologous recombination plasmid are known. Various methods for transforming bacteria with a plasmid are known, including heat-shock, F pilus mediated bacterial conjugation, electroporation, and other methods. Various methods for isolating a particular clone following homologous recombination are also known. Some method embodiments described herein utilize particular strategies.

Thus, some embodiments of methods for preparing indicator bacteriophage include the steps of selecting a wild-type bacteriophage that specifically infects a target pathogenic bacterium; determining the natural sequence in the late region of the genome of the selected bacteriophage; annotating the genome and identifying the major capsid protein gene of the selected bacteriophage; designing a sequence for homologous recombination adjacent to the major capsid protein gene, wherein the sequence comprises a codon-optimized reporter gene; incorporating the sequence designed for homologous recombination into a plasmid/vector; transforming the plasmid/vector into target pathogenic bacteria; selecting for the transformed bacteria; infecting the transformed bacteria with the selected wild-type bacteriophage, thereby allowing homologous recombination to occur between the plasmid and the bacteriophage genome; determining the titer of the resulting recombinant bacteriophage lysate; and performing a limiting dilution assay to enrich and isolate the recombinant bacteriophage. Some embodiments comprise further repeating the limiting dilution and titer steps, following the first limiting dilution assay, as needed until the recombinant bacteriophage represent a detectable fraction of the mixture. For example, in some embodiments the limiting dilution and titer steps can be repeated until at least 1/30 of the bacteriophage in the mixture are recombinant before isolating a particular clone of recombinant bacteriophage. A ratio of 1:30 recombinant: wild-type is expected to yield an average of 3.2 transducing units (TU) per 96 plaques (e.g., in a 96-well plate). By Poisson distribution, a 1:30 ratio therefore generates a 96% chance of observing at least one TU somewhere in the 96 wells.

FIG. 1 depicts a schematic representation of the wild-type CBA120 bacteriophage genome. The late gene cluster 110 was identified, and open reading frames 120 (ORF) in the late gene region were annotated. The ORF187/gp23 putative gene for the major capsid protein 130 (MCP) was identified and its sequence, along with downstream sequence in the late gene cluster, was used to prepare a recombinant plasmid carrying the desired reporter gene.

Some embodiments of methods of preparing a recombinant indicator bacteriophage include designing a plasmid that can readily recombine with the wild-type bacteriophage genome to generate recombinant genomes. In designing a plasmid, some embodiments include addition of a codon-optimized reporter gene, such as a luciferase gene. Some embodiments further include addition of elements into the upstream untranslated region. For example, in designing a plasmid to recombine with the CBA120 genome, an upstream untranslated region can be added between the sequence encoding the C-terminus of the gp23/Major Capsid Protein and the start codon of the NANOLUC® reporter gene. The untranslated region can include a promoter, such as a T4, T4-like, T7, T7-like, CBA120, ViI, or ViI-like promoter. The untranslated region can also include a Ribosomal Entry/Binding Site (RBS), also known as a "Shine-Dalgarno Sequence" with bacterial systems. Either or both of these elements, or other untranslated elements, can be embedded within a short upstream untranslated region made of random sequences comprising about the same GC content as rest of the phage genome. The random region should not include an ATG sequence, as that will act as a start codon.

There are numerous known methods and commercial products for preparing plasmids. For example PCR, site-directed mutagenesis, restriction digestion, ligation, cloning, and other techniques may be used in combination to prepare plasmids. Synthetic plasmids can also be ordered commercially (e.g., GeneWiz). Cosmids can also be employed, or the CRISPR/CAS9 system could be used to selectively edit a bacteriophage genome.

Figure 2:
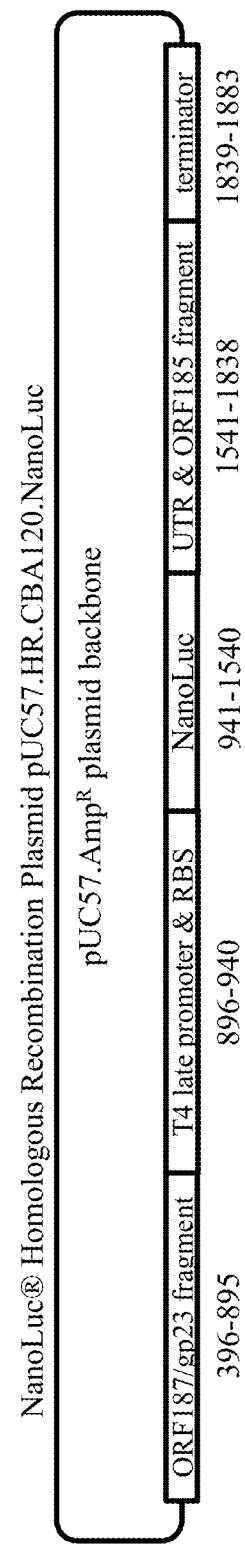
FIG. 2 shows one embodiment of a plasmid designed for homologous recombination with the CBA120 bacteriophage genome. Capsid protein gp23 (ORF187) is believed to represent the major capsid protein. As this virion protein is expressed at a very high level, any genes inserted into this region can be expected to have similar expression levels, as long as late gene promoters and/or other similar control elements are used.

FIG. 2 shows an embodiment of a plasmid designed to recombine with the CBA120 bacteriophage genome to generate a recombinant bacteriophage. This particular plasmid is designated pUC57.HR.CBA120.NanoLuc. The detection/indicator moiety is encoded by the NANOLUC® reporter gene 941-1540. The insert (396-1883) is in the standard AmpR version of pUC57. The major capsid protein C-terminal fragment is represented by 396-895, ORF187/gp23. A T4-like phage late promoter consensus sequence (902-912) & Shine-Dalgarno Ribosomal Entry/Binding Site (927-934) within the 5' untranslated region are represented by 896-940. The codon-optimized NANOLUC® reporter gene is represented by 941-1540. The untranslated region (UTR) and ORF185 hypothetical protein N-Terminal fragment are represented by 1541-1838. The transcriptional terminator (1839-1883) is only in the plasmid, and does not become part of the phage genome as a result of recombination.

The ORF187/gp23 fragment 396-895 is a part of a structural gene that encodes a virion protein. As these virion proteins are expressed at a very high level, any genes inserted into this region can be expected to have similar expression levels, as long as late gene promoters and/or other similar control elements are used.

Figure 3:
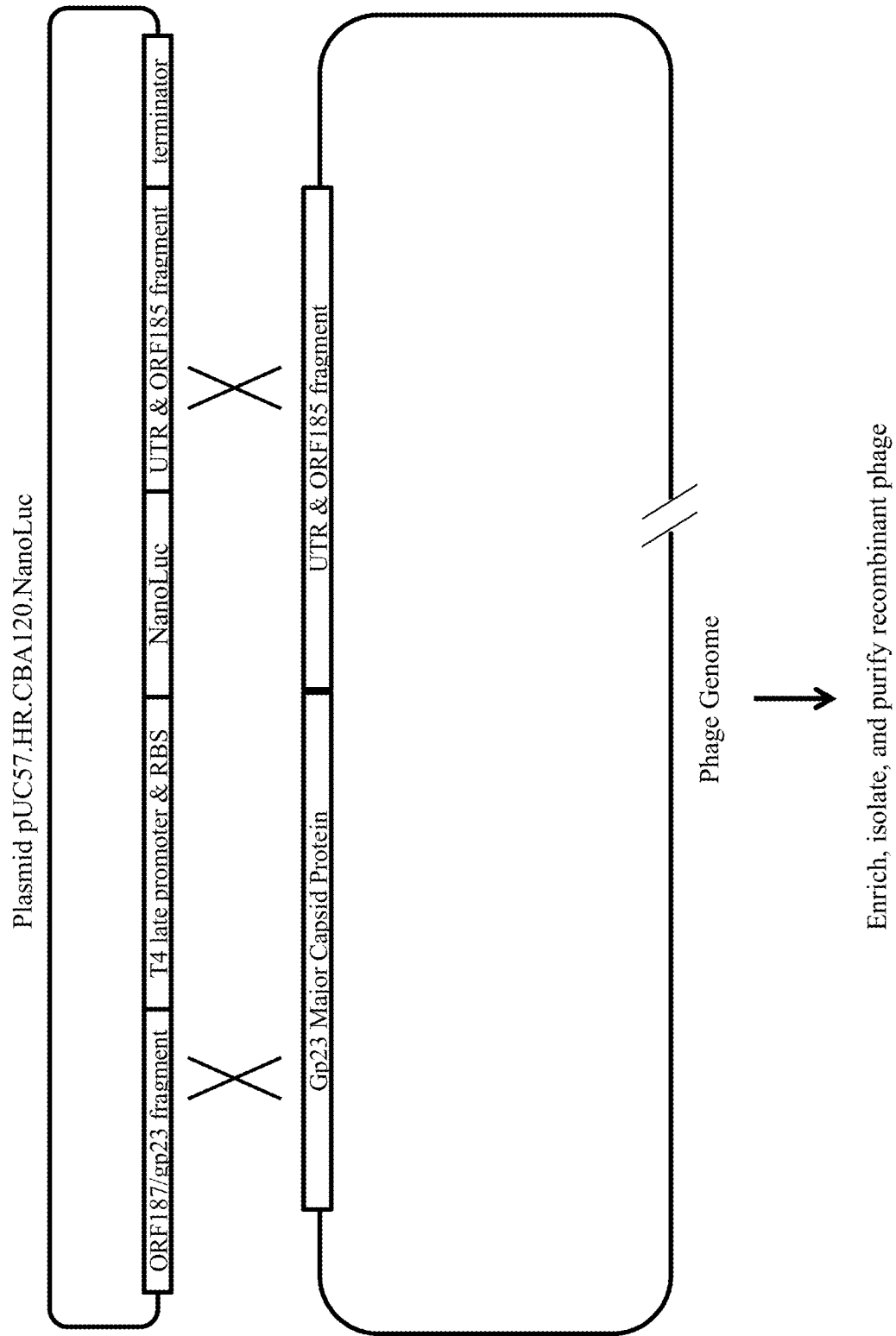
FIG. 3 shows an embodiment of homologous recombination of the wild-type CBA120 genome in FIG. 1 with the plasmid illustrated in FIG. 2.

FIG. 3 shows a schematic of the homologous recombination expected between the plasmid of FIG. 2 and bacteriophage genome of FIG. 1 to create recombinant bacteriophage that express the luciferase gene. In this embodiment of homologous recombination to generate recombinant bacteriophage, the CBA120 phage genome is 157,304 base pairs, while the synthesized plasmid is 4,117 base pairs. The final recombinant genome resulting from recombination is 157,949 base pairs.

In some embodiments, indicator phage according to the invention comprise CBA120 bacteriophage genetically engineered to comprise a reporter gene such as a luciferase gene. For example, an indicator phage can be the CBA120 bacteriophage wherein the genome comprises the sequence of the NANOLUC® gene. A recombinant CBA120 bacteriophage genome may further comprise a T4, T7, CBA120, ViI, or another late promoter.

Thus, in the embodiment of the recombinant phage generated as a result of the recombination illustrated in FIG. 3, the indicator gene (i.e., NANOLUC®) is inserted into the late gene region, just downstream of the gene encoding the major capsid protein, and thus creates recombinant bacteriophage genomes comprising the NANOLUC® gene. The construct may additionally comprise the consensus T4, T7, CBA120, ViI, or another late promoter or another suitable promoter to drive transcription and expression of the luciferase gene. The construct may also comprise a composite untranslated region synthesized from several UTRs. This construct ensures soluble luciferase is produced such that expression is not limited to the number of capsid proteins inherent in the phage display system.

Figure 4:
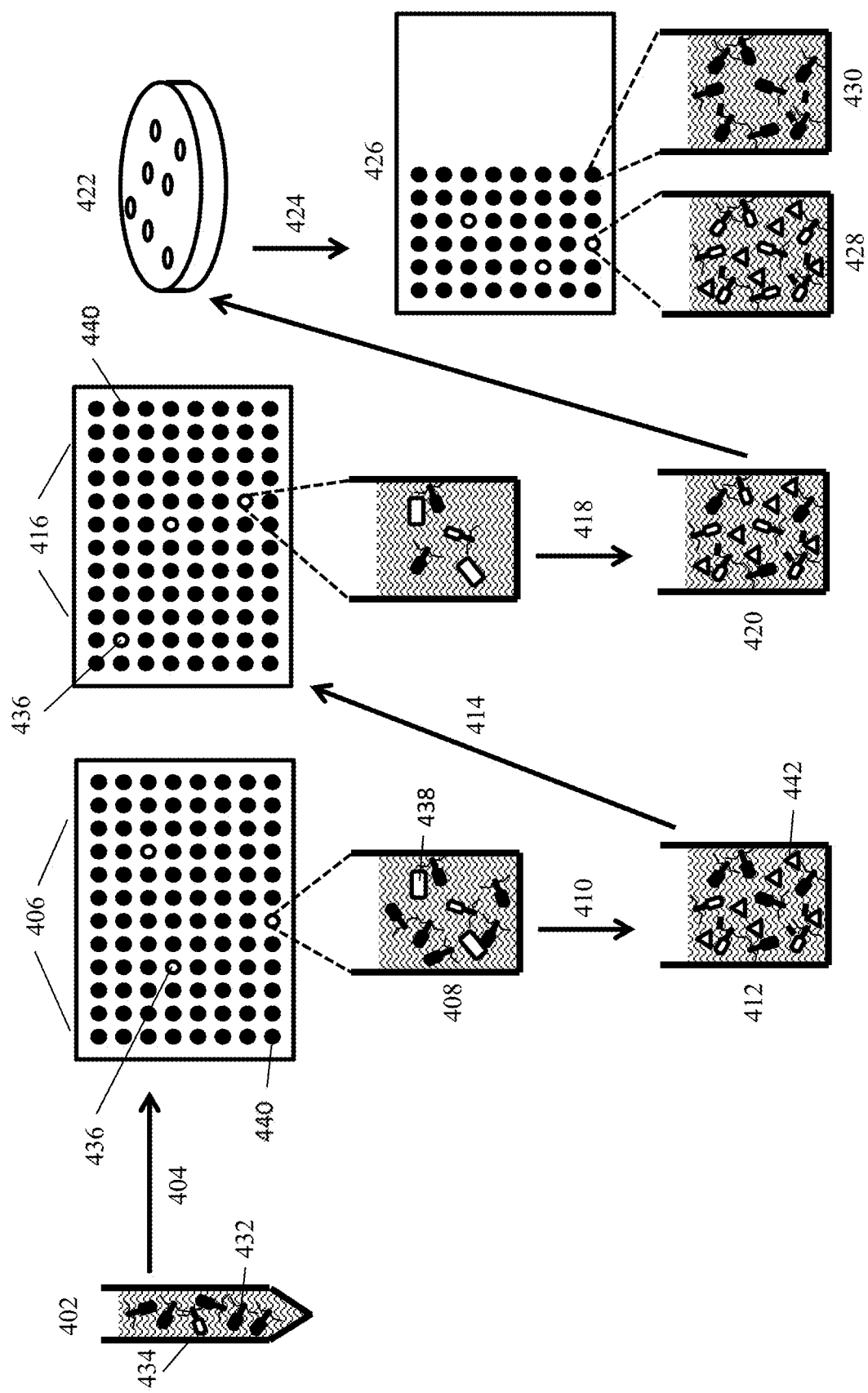
FIG. 4 depicts the isolation of recombinant bacteriophage from a mixture of wild-type and recombinant bacteriophage derived from transforming target bacteria with a plasmid carrying a sequence designed to recombine in homologous fashion with the natural bacteriophage genome, and then infecting the transformed bacteria with wild-type bacteriophage to allow homologous recombination. A series of sequential infection and dilution steps allow identification and isolation of recombinant phage that expresses an indicator/reporter gene.

FIG. 4 depicts the isolation of recombinant phage from the mixture of wild-type and recombinant bacteriophage resulting from the homologous recombination illustrated in FIG. 3, using the plasmid construct shown in FIG. 2.

In the first step 402, bacteria transformed with the homologous recombination plasmid are infected with bacteriophage, resulting in progeny phage with a mixture of parental and recombinant phage with a ratio of approximately 120 wild-type 432:1 recombinant phage 434. The resulting recombinant phage mix is diluted 404 into 96-well plates 406 to give an average of 3 recombinant transducing units (TU) per plate, which corresponds to about 3.8 infectious units (IU) of mostly wild-type phage per well. The 96-well plate is assayed for luciferase activity to identify wells 436 containing recombinant phage as compared to wells 440 containing wild-type bacteriophage. Bacteria 438 are added 408; for example, each well may contain about 50 µL of a turbid *E. coli* O157:H7 culture. This allows the phage to replicate and produce the luciferase enzyme 442. After 2 hours of incubation at 37° C. shown in 410, wells may be screened for the presence of luciferase 442. Any positive wells are likely to have been inoculated with a single recombinant phage, and at this stage the mixture may contain a ratio of approximately 3.8 wild-type phage:1 recombinant, an enrichment over the original 120:1 ratio. In one embodiment, soluble luciferase and phage were present at an approximate ratio of 16 wild-type:1 recombinant. If necessary (i.e., if the ratio of recombinant:wild-type is lower than 1:30), progeny from this enriched culture 412 may be subjected to additional limiting dilution assay(s) 414 to increase the ratio and determine the actual concentration of recombinant phage transducing units. For example, about 3 recombinant TU per 96-well plate 416 may be aliquoted 414 from the first purification stock, leading to an approximate inoculation of ~20 mostly wild-type phage per well of a second dilution assay plate 420. Any positive luciferase wells are likely to have been inoculated with a single recombinant along with ~20 wild-type phage. These wells may be analyzed for presence of luciferase 442.

After addition of bacteria and incubation (e.g., for 2 hours at 37° C.) 418, soluble luciferase and phage are present at approximately 20 wild-type:1 recombinant 420. Finally, a plaque assay may be performed 422 to screen for recombinants that express luciferase 446. A small number of individual (e.g., n=48) plaques may be individually picked and screened in a third multiwell plate 426 for luciferase activity 436. In an embodiment, this approach should insure that about 3 recombinants would be in the mix of plaques being screened. One plaque may be removed from the plate to each well of a 96-well plate 424 and a luciferase assay performed 426 to determine which wells contained phage exhibiting luciferase activity 442. Wells 428 demonstrating luciferase activity represent pure recombinant phage 434, while wells without luciferase activity 430 represent pure wild-type phage 432.

Individual plaques may then be suspended in buffer (e.g., 100 µL TMS) or media, and an aliquot (e.g., about 5 µL) added to a well containing a turbid *E. coli* O157:H7 culture, and assayed after incubation (e.g., about 45 minutes to 1 hour at 37° C.). Positive wells are expected to contain a pure culture of recombinant phage. Certain embodiments can include additional rounds of plaque purification.

Thus, as illustrated in FIG. 4, recombinant phage generated by homologous recombination of a plasmid designed for recombination with the wild-type phage genome can be isolated from a mixture comprising only 0.005% of total phage genomes. Following isolation, large scale production may be performed to obtain high titer recombinant indicator phage stocks appropriate for use in the *E. coli* O157:H7 detection assay. Furthermore, cesium chloride isopycnic density gradient centrifugation may be used to separate phage particles from contaminating luciferase protein to reduce background.

Figure 5:
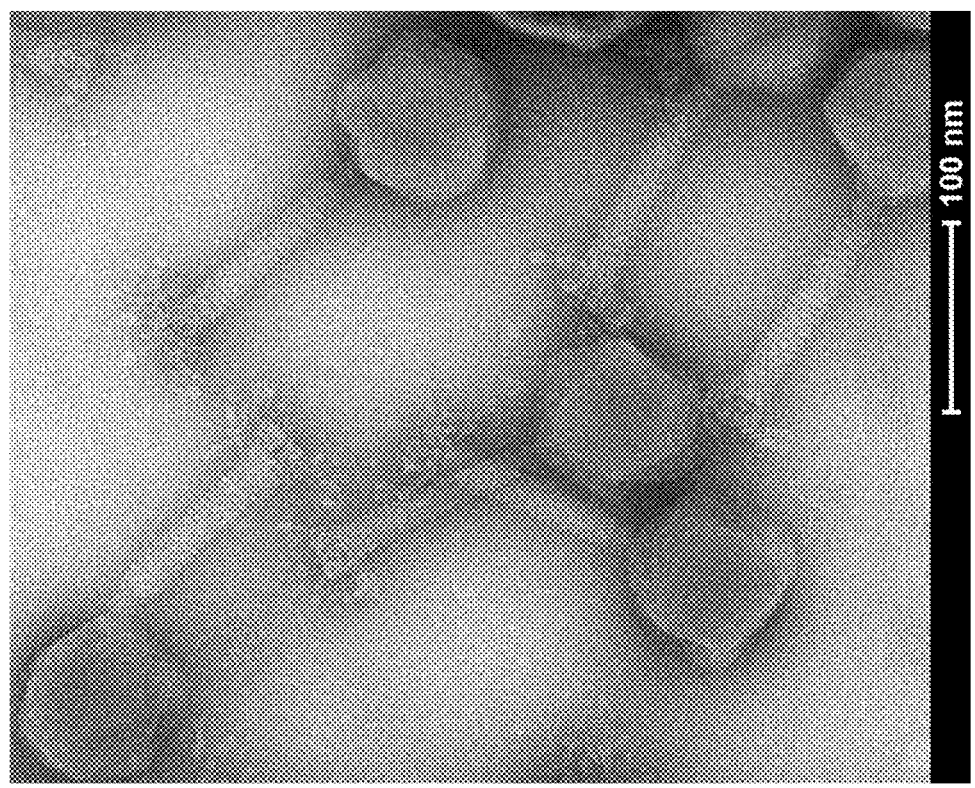
FIG. 5 is an electron micrograph of one embodiment of a recombinant indicator bacteriophage, the CBA120NanoLuc bacteriophage.

FIG. 5 shows an electron micrograph of one embodiment of a recombinant indicator bacteriophage generated by recombination of the wild-type CBA120 bacteriophage genome shown in FIG. 1 with the plasmid shown in FIG. 2, as illustrated in FIG. 3. To capture the image, the bacteriophage purified on a 5-20% sucrose density gradient were adsorbed onto a glow discharge-treated carbon film and stained with 2% uranyl acetate. The sample was viewed in a FEI Tecnai $G^2$ Spirit BioTwin Transmission Electron Microscope and the micrograph taken with an Eagle™ 2K CCD. This indicator bacteriophage is designated "CBA120NanoLuc" (or "CBA120NanoLuc indicator phage") and was utilized in the assays described herein. The data presented in Examples and Figures herein were obtained using this Indicator Phage for infection of bacteria in the sample being tested.

In this way, and as described in more detail in the Examples below, recombinant bacteriophage having the reporter gene of interest (e.g., luciferase gene such as Firefly, *Oplophorus* or an engineered luciferase such as NANO-LUC®) inserted into a wild-type bacteriophage may be generated.

Methods of Using Infectious Agents for Detecting Microorganisms

As noted herein, in certain embodiments, the invention may comprise methods of using infectious particles for detecting microorganisms. The methods of the invention may be embodied in a variety of ways.

In an embodiment, the invention may comprise a method for detecting a bacterium of interest in a sample comprising the steps of: incubating the sample with bacteriophage that infects the bacterium of interest, wherein the bacteriophage comprises an indicator gene such that expression of the indicator gene during bacteriophage replication following infection of the bacterium of interest results in production of a soluble indicator protein product; and detecting the indicator protein product, wherein positive detection of the indicator protein product indicates that the bacterium of interest is present in the sample.

In certain embodiments, the assay may be performed to utilize a general concept that can be modified to accommodate different sample types or sizes and assay formats. Embodiments employing recombinant bacteriophage of the invention (i.e., indicator bacteriophage) may allow rapid detection of specific bacterial strains, with total assay times under 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, or 12 hours, depending on the sample type, sample size, and assay format. For example, the amount of time required may be somewhat shorter or longer depending on the strain of bacteriophage and the strain of bacteria to be detected in the assay, type and size of the sample to be tested, conditions required for viability of the target, complexity of the physical/chemical environment, and the concentration of "endogenous" non-target bacterial contaminants.

Figure 6:
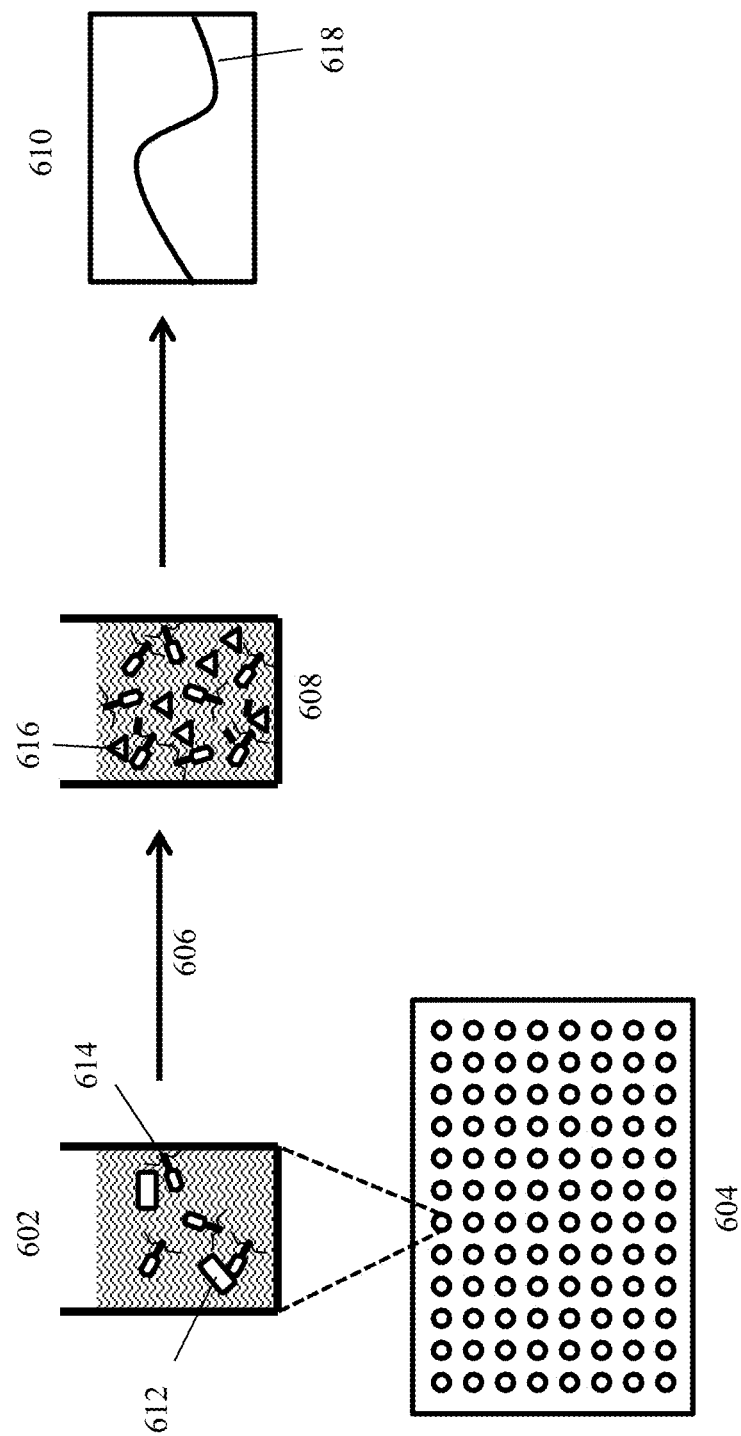
FIG. 6 depicts the use of indicator bacteriophage encoding a soluble reporter (e.g., luciferase) to detect bacterial cells via detection of luciferase generated from replication of indicator bacteriophage during infection of the bacterial cells, according to an embodiment of the invention.

FIG. 6 illustrates an embodiment of an assay for detecting a bacterium of interest using a modified bacteriophage according to an embodiment of the invention. Aliquots of indicator phage 614 are distributed to the individual wells 602 of a multi-well plate 604, and then test sample aliquots containing bacteria 612 are added and incubated 606 for a period of time (e.g., 45 minutes at 37° C.) sufficient for phage to replicate and generate soluble indicator 616 (e.g., luciferase). The plate wells 608 containing soluble indicator and phage may then be assayed 610 to measure the indicator activity on the plate 618 (e.g., luciferase assay). Experiments utilizing this method are described herein. In some embodiments, the test samples are not concentrated (e.g., by centrifugation) but are incubated directly with indicator phage for a period of time and subsequently assayed for luciferase activity. In other embodiments, various tools (e.g., a centrifuge or filter) may be used to concentrate the samples before enrichment or before testing. For example, a 10 mL aliquot of a prepared sample may be extracted and centrifuged to pellet cells and large debris. The pellet can be resuspended in a smaller volume for enrichment or for testing (i.e., before infecting the sample with Indicator Bacteriophage).

In some embodiments, the sample may be enriched prior to testing by incubation in conditions that encourage growth. In such embodiments, the enrichment period can be 1, 2, 3, 4, 5, 6, 7, or up to 8 hours or longer, depending on the sample type and size.

Thus, in some embodiments, the indicator bacteriophage comprises a detectable indicator moiety, and infection of a single pathogenic cell (e.g., bacterium) can be detected by an amplified signal generated via the indicator moiety. Thus the method may comprise detecting an indicator moiety produced during phage replication, wherein detection of the indicator indicates that the bacterium of interest is present in the sample.

In an embodiment, the invention may comprise a method for detecting a bacterium of interest in a sample comprising the steps of: incubating the sample with a recombinant bacteriophage that infects the bacterium of interest, wherein the recombinant bacteriophage comprises an indicator gene inserted into a late gene region of the bacteriophage such that expression of the indicator gene during bacteriophage replication following infection of host bacteria results in production of a soluble indicator protein product; and detecting the indicator protein product, wherein positive detection of the indicator protein product indicates that the bacterium of interest is present in the sample. In some embodiments, the amount of indicator moiety detected corresponds to the amount of the bacterium of interest present in the sample.

As described in more detail herein, the methods and systems of the invention may utilize a range of concentrations of parental indicator bacteriophage to infect bacteria present in the sample. In some embodiments the indicator bacteriophage are added to the sample at a concentration sufficient to rapidly find, bind, and infect target bacteria that are present in very low numbers in the sample, such as a single cell. In some embodiments, the phage concentration can be sufficient to find, bind, and infect the target bacteria in less than one hour. In other embodiments, these events can occur in less than two hours, or less than three hours, following addition of indicator phage to the sample. For example, in certain embodiments, the bacteriophage concentration for the incubating step is greater than $1\times10^5$ PFU/mL, greater than $1\times10^6$ PFU/mL, or greater than $1\times10^7$ PFU/mL.

In certain embodiments, the recombinant infectious agent may be purified so as to be free of any residual indicator protein that may be generated upon production of the infectious agent stock. Thus, in certain embodiments, the recombinant bacteriophage may be purified using cesium chloride isopycnic density gradient centrifugation prior to incubation with the sample. When the infectious agent is a bacteriophage, this purification may have the added benefit of removing bacteriophage that do not have DNA (i.e., empty phage or "ghosts").

In some embodiments of the methods of the invention, the microorganism may be detected without any isolation or purification of the microorganisms from a sample. For example, in certain embodiments, a sample containing one or a few microorganisms of interest may be applied directly to an assay container such as a spin column, a microtiter well, or a filter and the assay is conducted in that assay container. Various embodiments of such assays are disclosed herein.

Aliquots of a test sample may be distributed directly into wells of a multi-well plate, indicator phage may be added, and after a period of time sufficient for infection, a lysis buffer may be added as well as a substrate for the indicator moiety (e.g., luciferase substrate for a luciferase indicator) and assayed for detection of the indicator signal. Some embodiments of the method can be performed on filter plates. Some embodiments of the method can be performed with or without concentration of the sample before infection with indicator phage.

For example, in many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Methods of the invention may comprise various other steps to increase sensitivity. For example, as discussed in more detail herein, the method may comprise a step for washing the captured and infected bacterium, after adding the bacteriophage but before incubating, to remove excess parental bacteriophage and/or luciferase or other reporter protein contaminating the bacteriophage preparation.

In some embodiments, detection of the microorganism of interest may be completed without the need for culturing the sample as a way to increase the population of the microorganisms. For example, in certain embodiments the total time required for detection is less than 12.0 hours, 11.0 hours, 10.0 hours, 9.0 hours, 8.0 hours, 7.0 hours, 6.0 hours, 5.0 hours, 4.0 hours, 3.0 hours, 2.5 hours, 2.0 hours, 1.5 hours, 1.0 hour, 45 minutes, or less than 30 minutes. Minimizing time to result is critical in food and environmental testing for pathogens.

In contrast to assays known in the art, the method of the invention can detect individual microorganisms. Thus, in certain embodiments, the method may detect<10 cells of the microorganism (i.e., 1, 2, 3, 4, 5, 6, 7, 8, 9 microorganisms) present in a sample. For example, in certain embodiments, the recombinant bacteriophage is highly specific for *E. coli* O157:H7. In an embodiment, the recombinant bacteriophage can distinguish *E. coli* O157:H7 in the presence of more than 100 other types of bacteria. In certain embodiments, the recombinant bacteriophage can be used to detect a single bacterium of the specific type in the sample. In certain embodiments, the recombinant bacteriophage detects as few as 2, 3, 4, 5, 6, 7, 8, 9, 10, 15, 20, 30, 40, 50, 60, 70, 80, 90, or 100 of the specific bacteria in the sample.

Thus, aspects of the present invention provide methods for detection of microorganisms in a test sample via an indicator moiety. In some embodiments, where the microorganism of interest is a bacterium, the indicator moiety may be associated with an infectious agent such as an indicator bacteriophage. The indicator moiety may react with a substrate to emit a detectable signal or may emit an intrinsic signal (e.g., fluorescent protein). In some embodiments, the detection sensitivity can reveal the presence of as few as 50, 20, 10, 9, 8, 7, 6, 5, 4, 3, or 2 cells of the microorganism of interest in a test sample. In some embodiments, even a single cell of the microorganism of interest may yield a detectable signal. In some embodiments, the bacteriophage is a T4-like or ViI-like bacteriophage. In some embodiments, the recombinant bacteriophage is derived from CBA120. In certain embodiments, a CBA120 recombinant bacteriophage is highly specific for E. coli O157:H7.

In some embodiments, the indicator moiety encoded by the infectious agent may be detectable during or after replication of the infectious agent. Many different types of detectable biomolecules suitable for use as indicator moieties are known in the art, and many are commercially available. In some embodiments the indicator phage comprises an enzyme, which serves as the indicator moiety. In some embodiments, the genome of the indicator phage is modified to encode a soluble protein. In some embodiments, the indicator phage encodes a detectable enzyme. The indicator may emit light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, Oplophorus luciferase is the indicator moiety. In some embodiments, NANOLUC® is the indicator moiety. Other engineered luciferases or other enzymes that generate detectable signals may also be appropriate indicator moieties.

Thus, in some embodiments, the recombinant bacteriophage of the methods, systems or kits is prepared from wild-type bacteriophage CBA120. In some embodiments, the indicator gene encodes a protein that emits an intrinsic signal, such as a fluorescent protein (e.g., green fluorescent protein or others). The indicator may emit light and/or may be detectable by a color change. In some embodiments, the indicator gene encodes an enzyme (e.g., luciferase) that interacts with a substrate to generate signal. In some embodiments, the indicator gene is a luciferase gene. In some embodiments, the luciferase gene is one of Oplophorus luciferase, Firefly luciferase, Renilla luciferase, External Gaussia luciferase, Lucia luciferase, or an engineered luciferase such as NANOLUC®, Rluc8.6-535, or Orange Nano-lantern.

Detecting the indicator may include detecting emissions of light. In some embodiments, a luminometer may be used to detect the reaction of indicator (e.g., luciferase) with a substrate. The detection of RLU can be achieved with a luminometer, or other machines or devices may also be used. For example, a spectrophotometer, CCD camera, or CMOS camera may detect color changes and other light emissions. Absolute RLU are important for detection, but the signal to background ratio also needs to be high (e.g., >2.0, >2.5, or >3.0) in order for single cells or low numbers of cells to be detected reliably.

In some embodiments, the indicator phage is genetically engineered to contain the gene for an enzyme, such as a luciferase, which is only produced upon infection of bacteria that the phage specifically recognizes and infects. In some embodiments, the indicator moiety is expressed late in the viral life cycle. In some embodiments, as described herein, the indicator is a soluble protein (e.g., soluble luciferase) and is not fused with a phage structural protein that limits its copy number.

Thus in some embodiments utilizing indicator phage, the invention comprises a method for detecting a microorganism of interest comprising the steps of capturing at least one sample bacterium; incubating the at least one bacterium with a plurality of indicator phage; allowing time for infection and replication to generate progeny phage and express soluble indicator moiety; and detecting the progeny phage, or preferably the indicator, wherein detection of the indicator demonstrates that the bacterium is present in the sample.

For example, in some embodiments the test sample bacterium may be captured by binding to the surface of a plate, or by filtering the sample through a bacteriological filter (e.g., 0.45 µm pore size spin filter or plate filter). In an embodiment, the infectious agent (e.g., indicator phage) is added in a minimal volume to the captured sample directly on the filter. In an embodiment, the microorganism captured on the filter or plate surface is subsequently washed one or more times to remove excess unbound infectious agent. In an embodiment, a medium (e.g., Luria-Bertani Broth, also called LB herein, or Tryptic Soy Broth or Tryptone Soy Broth, also called TSB herein) may be added for further incubation time, to allow replication of bacterial cells and phage and high-level expression of the gene encoding the indicator moiety. However, a surprising aspect of some embodiments of testing assays is that the incubation step with indicator phage only needs to be long enough for a single phage life cycle. The amplification power of using bacteriophage was previously thought to require more time, such that the phage would replicate for several cycles. A single replication cycle of indicator phage can be sufficient to facilitate sensitive and rapid detection according to some embodiments of the present invention.

In some embodiments, aliquots of a test sample comprising bacteria may be applied to a spin column and after infection with a recombinant bacteriophage and an optional washing to remove any excess bacteriophage, the amount of soluble indicator detected will be proportional to the amount of bacteriophage that are produced by infected bacteria.

Soluble indicator (e.g., luciferase) released into the surrounding liquid upon lysis of the bacteria may then be measured and quantified. In an embodiment, the solution is spun through the filter, and the filtrate collected for assay in a new receptacle (e.g., in a luminometer) following addition of a substrate for the indicator enzyme (e.g., luciferase substrate). Alternatively, the indicator signal may be measured directly on the filter.

In various embodiments, the purified parental indicator phage does not comprise the detectable indicator itself, because the parental phage can be purified before it is used for incubation with a test sample. Expression of late (Class III) genes occurs late in the viral life cycle. In some embodiments of the present invention, parental phage may be purified to exclude any existing indicator protein (e.g., luciferase). In some embodiments, expression of the indicator gene during bacteriophage replication following infection of host bacteria results in a soluble indicator protein product. Thus, in many embodiments, it is not necessary to separate parental from progeny phage prior to the detecting step. In an embodiment, the microorganism is a bacterium and the indicator phage is a bacteriophage. In an embodiment, the indicator moiety is soluble luciferase, which is released upon lysis of the host microorganism.

Thus, in an alternate embodiment, the indicator substrate (e.g., luciferase substrate) may be incubated with the portion of the sample that remains on a filter or bound to a plate surface. Accordingly, in some embodiments the solid support is a 96-well filter plate (or regular 96-well plate), and the substrate reaction may be detected by placing the plate directly in the luminometer.

For example, in an embodiment, the invention may comprise a method for detecting *E. coli* O157:H7 comprising the steps of: infecting cells captured on a 96-well filter plate with a plurality of parental indicator phage capable of expressing luciferase upon infection; washing excess phage away; adding LB broth and allowing time for phage to replicate and lyse the specific *E. coli* target (e.g., 30-90 minutes); and detecting the indicator luciferase by adding luciferase substrate and measuring luciferase activity directly in the 96-well plate, wherein detection of luciferase activity indicates that the *E. coli* O157:H7 is present in the sample.

In another embodiment, the invention may comprise a method for detecting *E. coli* O157:H7 comprising the steps of: infecting cells in liquid solution or suspension in a 96-well plate with a plurality of parental indicator phage capable of expressing luciferase upon infection; allowing time for phage to replicate and lyse the specific *E. coli* target (e.g., 30-120 minutes); and detecting the indicator luciferase by adding luciferase substrate and measuring luciferase activity directly in the 96-well plate, wherein detection of luciferase activity indicates that the *E. coli* O157:H7 is present in the sample. In such an embodiment no capturing step is necessary. In some embodiments, the liquid solution or suspension may be a consumable test sample, such as a vegetable wash. In some embodiments, the liquid solution or suspension may be vegetable wash fortified with concentrated LB Broth, Tryptic/Tryptone Soy Broth, Peptone Water or Nutrient Broth. In some embodiments, the liquid solution or suspension may be bacteria diluted in LB Broth.

In some embodiments, lysis of the bacterium may occur before, during, or after the detection step. Experiments suggest that infected unlysed cells may be detectable upon addition of luciferase substrate in some embodiments. Presumably, luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with sample in solution or suspension, where the original plate full of intact and lysed cells is directly assayed in the luminometer, lysis is not necessary for detection.

In some embodiments, the reaction of indicator moiety (e.g., luciferase) with substrate may continue for 30 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of phage utilized for infecting test samples have successfully achieved detection of very low numbers of target microorganism in a very short timeframe. The incubation of phage with a test sample in some embodiments need only be long enough for a single phage life cycle. In some embodiments, the bacteriophage concentration for this incubating step is greater than $7\times10^6$, $8\times10^6$, $9\times10^6$, $1.0\times10^7$, $1.1\times10^7$, $1.2\times10^7$, $1.3\times10^7$ $1.4\times10^7$ $1.5\times10^7$ $1.6\times10^7$ $1.7\times10^7$ $1.8\times10^7$ $1.9\times10^7$ $2.0\times10^7$ $3.0\times10^7$ $4.0\times10^7$ $5.0\times10^7$, $6.0\times10^7$, $7.0\times10^7$, $8.0\times10^7$, $9.0\times10^7$, or $1.0\times10^8$ PFU/mL.

Success with such high concentrations of phage is surprising because the large numbers of phage were previously associated with "lysis from without," which killed target cells and thereby prevented generation of useful signal from earlier phage assays. It is possible that the clean-up of prepared phage stocks described herein helps to alleviate this problem (e.g., clean-up by cesium chloride isopycnic density gradient ultracentrifugation), because in addition to removing any contaminating luciferase associated with the phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude phage lysate (i.e., before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a very clean phage prep allows the assay to be performed with no wash steps, which makes the assay possible to perform without an initial concentration step. Some embodiments do include an initial concentration step, and in some embodiments this concentration step allows a shorter enrichment incubation time.

Some embodiments of testing methods may further include confirmatory assays. A variety of assays are known in the art for confirming an initial result, usually at a later point in time. For example, the samples can be cultured (e.g., CHROMAGAR®/DYNABEADS® assay as described in Example 4), PCR can be utilized to confirm the presence of the microbial DNA, or other confirmatory assays can be used to confirm the initial result.

Figure 7:
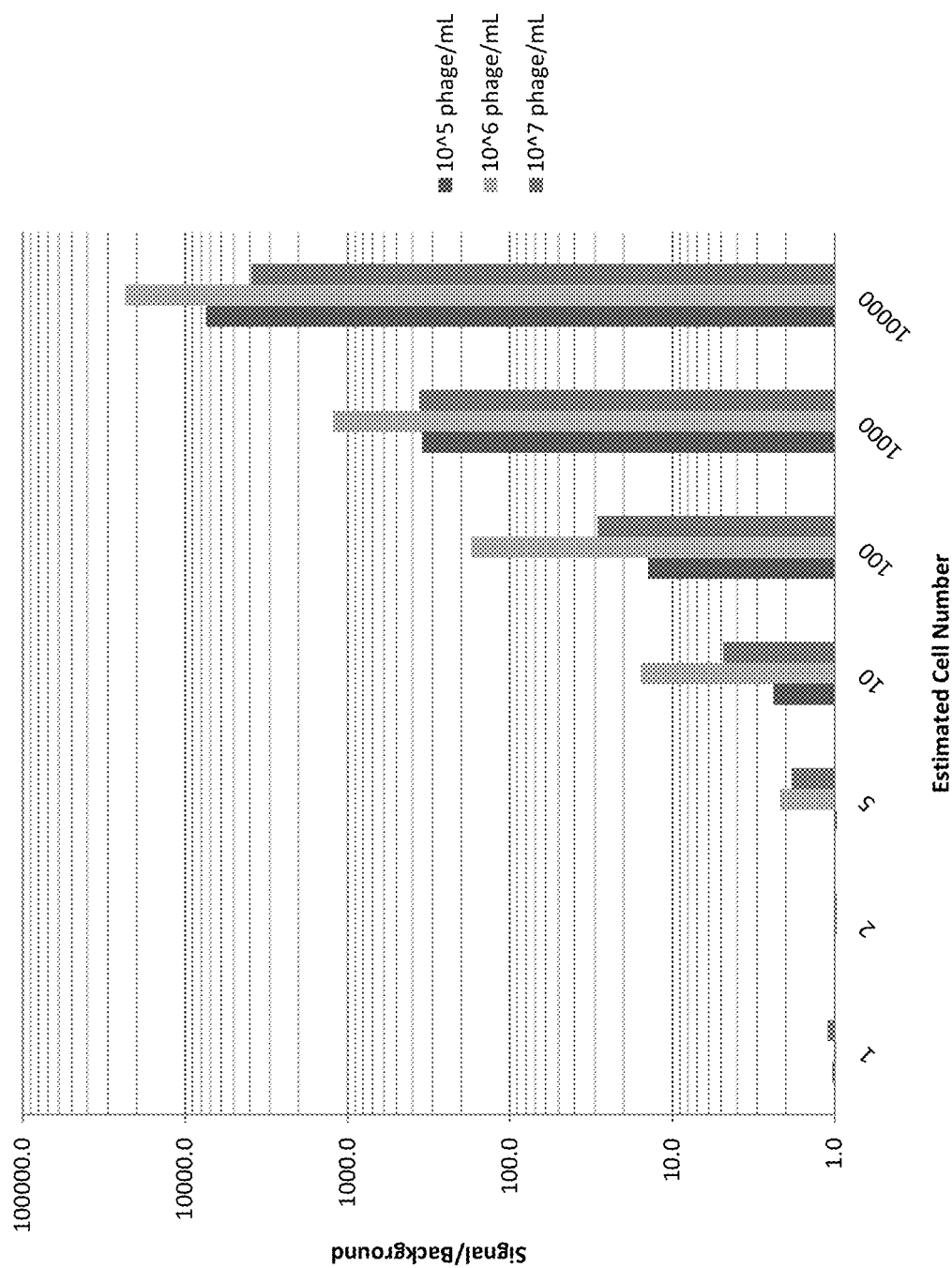
FIG. 7 demonstrates the detection of pathogenic bacteria using different phage concentrations of CBA120NanoLuc for infecting samples with known numbers of cells, with $10^6$ phage/mL yielding the highest signal to background ratio.
Figure 8:
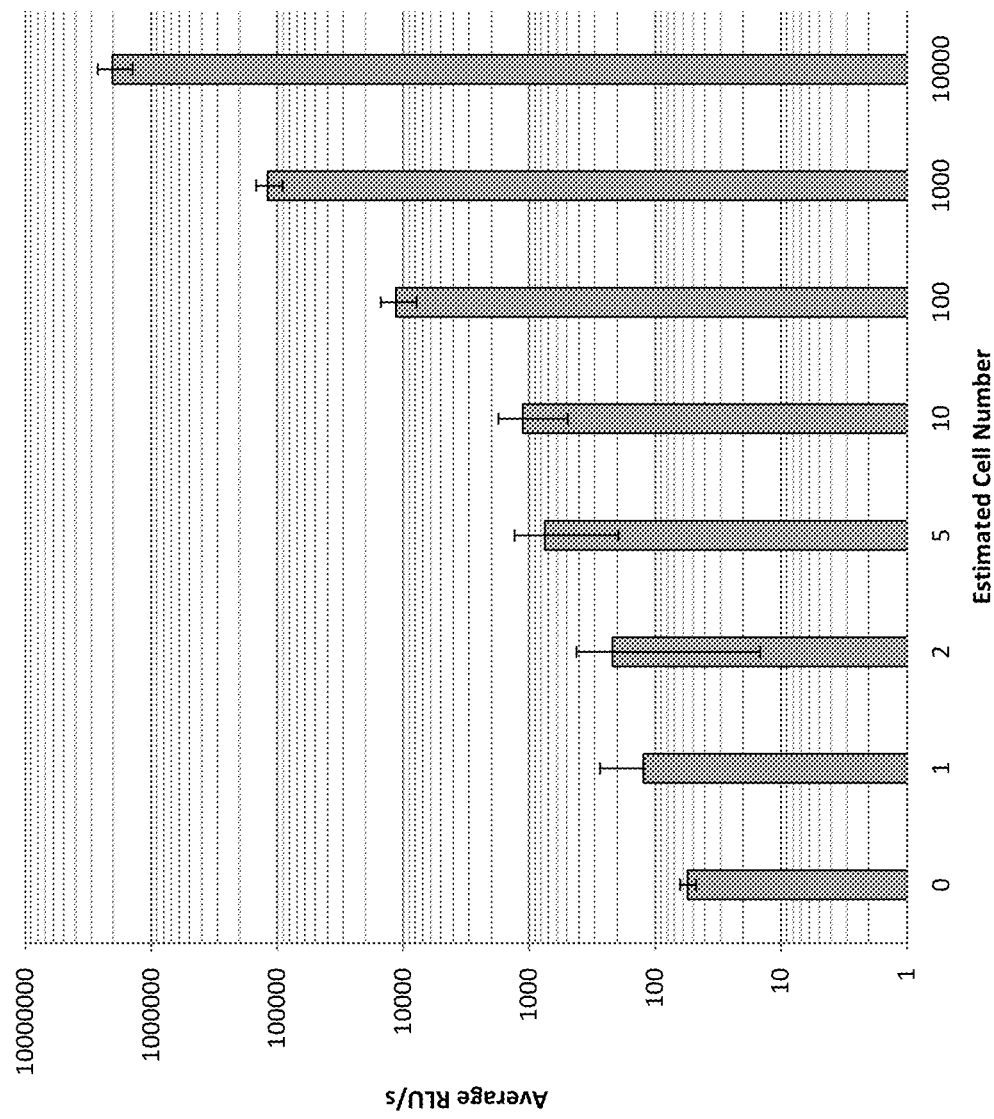
FIG. 8 demonstrates that replicates of experiments using $10^6$ phage/mL CBA120NanoLuc for infecting samples with known numbers of cells show significant differences between signal from a single cell and signal from 0 cells, 2 cells, or more.
Figure 9:
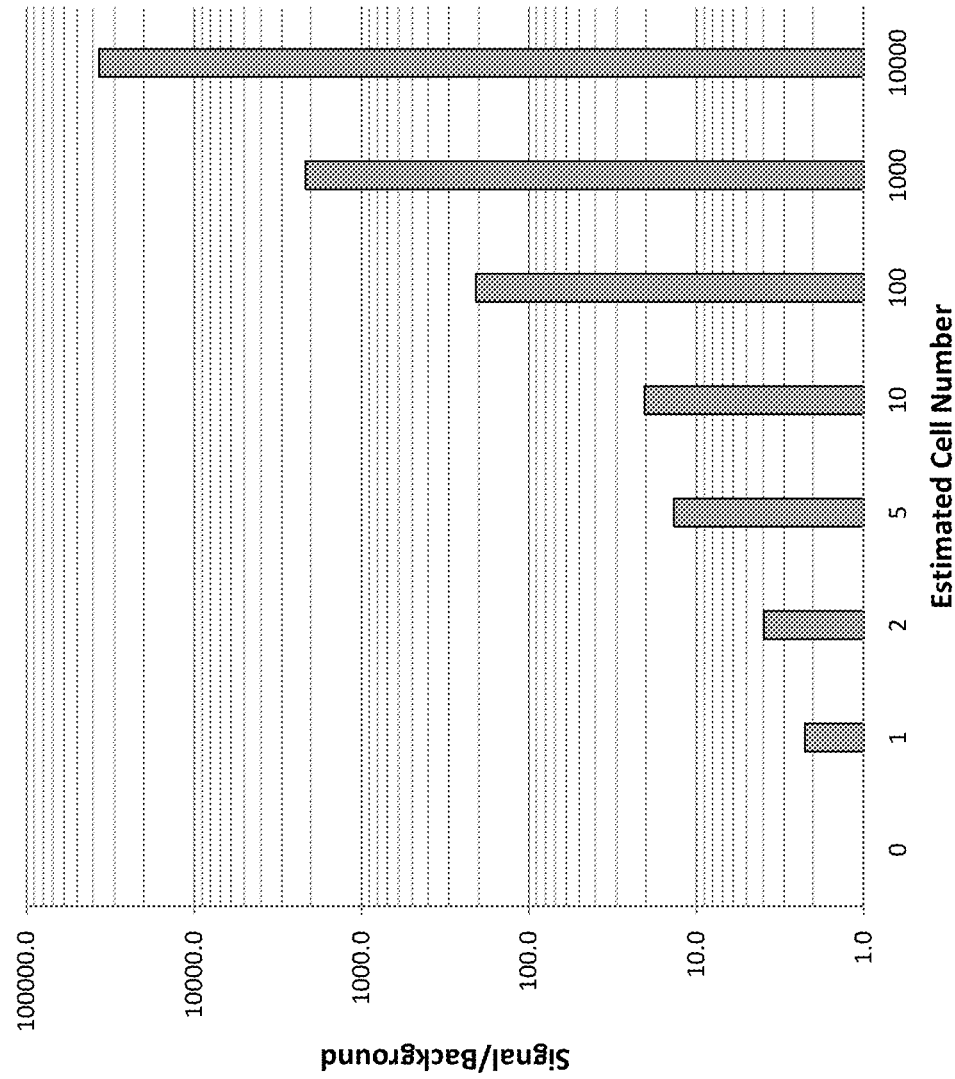
FIG. 9 demonstrates that the signal to background ratio for the experiment shown in FIG. 8 is greater than 2.0.

FIGS. 7-9 demonstrate data from basic assays (e.g., performed as shown in FIG. 6) on samples derived from *E. coli* O157:H7 cultures, using the CBA120NanoLuc Indicator Phage. FIG. 7 demonstrates three different infecting phage concentrations, $10^5$, $10^6$, and $10^7$ phage/mL. FIG. 8 uses 6-10 replicates of each indicated cell number to demonstrate significant differences between signals from single cells as compared to zero cells (background) or higher numbers of cells. FIG. 9 shows that the signal to background ratio for the experiment shown in FIG. 8 is greater than 2.0. Example 3 also describes these experiments.

Beef Assays

Existing protocols for detection of *E. coli* O157:H7 in foods are complicated, expensive, slow, labor-intensive and prone for false positives. Detection with a recombinant bacteriophage specific for this pathogen offers an effective, fast and simple testing alternative.

Embodiments of beef assays include sample preparation steps. Some embodiments can include enrichment time. For example, enrichment for 1, 2, 3, 4, 5, 6, 7, or 8 hours may be needed, depending on sample type and size. Following these sample preparation steps, infection with a high concentration of recombinant bacteriophage that expresses a reporter or indicator can be performed in a variety of assay formats, such as that shown in FIG. 6.

Embodiments of beef assays can detect a single pathogenic bacterium in sample sizes corresponding to industry standards, with a reduction in time-to-results of 20-50%, depending on the sample type and size.

FIGS. 10-16 show data from beef assay experiments using CBA120NanoLuc Indicator Bacteriophage, as described in Example 4.

Vegetable Wash Assays

To prepare the vegetable wash, vegetable leaves (e.g., spinach or lettuce) may be weighed and added to a clean plastic bag. Liquid can be added to the vegetable wash. For example, in some embodiments 5 mL of water are added per each gram (g) of vegetable. Other laboratory liquids (e.g., LB) may also be used. Leaves and solution can be mixed manually for a few minutes. Liquid can then be extracted from the plastic bag and can be used as the "vegetable wash." Using this method, ~1 million "endogenous" bacterial contaminants were found to reside on a single spinach leaf (1-2 g).

The assay is quantitative in that the signal detected is proportional to the amount of the bacterium of interest in the sample. For example, known numbers of $E.$ $coli$ O157:H7 cells can be added to vegetable wash samples to simulate contamination of vegetables with pathogenic bacteria. The experiment using vegetable wash samples described in Example 5 demonstrates marked differences between the signal from 0 cells, 1 cell, and 7 cells per assay, demonstrating the ability to detect single-digit cell numbers in vegetable wash. Using more bacterial cells per assay shows increasing signal in a dose-dependent manner. The vegetable wash contains about $10^6$ non-target bacteria/mL, corresponding to at least $10^5$ non-target bacteria per sample in this assay (including the 0 cells $E.$ $coli$ O157:H7 control). The ability to discern as few as a single target bacterial cell from $10^5$ non-target bacteria is surprising and again demonstrates the specificity and sensitivity of the assay. FIG. 17 shows data from a vegetable wash experiment (Example 5).

In some embodiments, the incubating step of the methods described herein comprises a final bacteriophage concentration of greater than $7 \times 10^6$, $8 \times 10^6$, $9 \times 10^6$, $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $3.0 \times 10^7$, $4.0 \times 10^7$, $5.0 \times 10^7$, $6.0 \times 10^7$, $7.0 \times 10^7$, $8.0 \times 10^7$, $9.0 \times 10^7$, or $1.0 \times 10^8$ PFU/mL. Such high phage concentrations were previously reported to be detrimental to such an assay, and therefore successful use of such high concentrations generated unexpected results. In some embodiments, the methods of the invention require less than 12, 11, 10, 9, 8, 7, 6, 5, 4, 3, or 2 hours for detection of a microorganism of interest. In some embodiments, the methods can detect as few as 100, 50, 20, 10, 9, 8, 7, 6, 5, 4, 3, or 2 cells of the bacterium of interest. These are shorter timeframes than were previously thought possible. In some embodiments, even a single cell of the bacterium is detectable. In additional embodiments, the invention comprises systems (e.g., computer systems, automated systems or kits) comprising components for performing the methods disclosed herein, and/or using the modified bacteriophage described herein.

Systems and Kits of the Invention

In some embodiments, the invention comprises systems (e.g., automated systems or kits) comprising components for performing the methods disclosed herein. In some embodiments, indicator phage are comprised in systems or kits according to the invention. Methods described herein may also utilize such indicator phage systems or kits. Some embodiments described herein are particularly suitable for automation and/or kits, given the minimal amount of reagents and materials required to perform the methods. In certain embodiments, each of the components of a kit may comprise a self-contained unit that is deliverable from a first site to a second site.

In some embodiments, the invention comprises systems or kits for rapid detection of a microorganism of interest in a sample. The systems or kits may in certain embodiments comprise a component for incubating the sample with an infectious agent specific for the microorganism of interest, wherein the infectious agent comprises an indicator moiety and a component for detecting the indicator moiety. In some embodiments of both the systems and the kits of the invention, the infectious agent is a recombinant bacteriophage that infects the bacterium of interest, and the recombinant bacteriophage comprises an indicator gene inserted into a late gene region of the bacteriophage as the indicator moiety such that expression of the indicator gene during bacteriophage replication following infection of host bacteria results in a soluble indicator protein product. Some systems further comprise a component for capturing the microorganism of interest on a solid support.

In other embodiments, the invention comprises a method, system, or kit for rapid detection of a microorganism of interest in a sample, comprising an infectious agent component that is specific for the microorganism of interest, wherein the infectious agent comprises an indicator moiety, and a component for detecting the indicator moiety. In some embodiments, the bacteriophage is a T4-like, ViI, ViI-like, or CBA120 bacteriophage. In one embodiment, the recombinant bacteriophage is derived from CBA120. In certain embodiments, the recombinant bacteriophage is highly specific for a particular bacterium. For example, in certain embodiments, the recombinant bacteriophage is highly specific for $E.$ $coli$ O157:H7. In an embodiment, the recombinant bacteriophage can distinguish $E.$ $coli$ O157:H7 in the presence of more than 100 other types of bacteria. In certain embodiments, a system or kit detects a single bacterium of the specific type in the sample. In certain embodiments, a system or kit detects as few as 2, 3, 4, 5, 6, 7, 8, 9, 10, 15, 20, 30, 40, 50, 60, 70, 80, 90, or 100 specific bacteria in the sample.

In certain embodiments, the systems and/or kits may further comprise a component for washing the captured microorganism sample. Additionally or alternatively, the systems and/or kits may further comprise a component for determining amount of the indicator moiety, wherein the amount of indicator moiety detected corresponds to the amount of microorganism in the sample. For example, in certain embodiments, the system or kit may comprise a luminometer or other device for measuring a luciferase enzyme activity.

In some systems and/or kits, the same component may be used for multiple steps. In some systems and/or kits, the steps are automated or controlled by the user via computer input and/or wherein a liquid-handling robot performs at least one step.

Thus in certain embodiments, the invention may comprise a system or kit for rapid detection of a microorganism of interest in a sample, comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing (e.g., a filter component). Some embodiments additionally comprise a component for determining amount of the microorganism of interest in the sample, wherein the amount of indicator moiety detected corresponds to the amount of microorganism in the sample. Such systems can include various embodiments and subembodiments analogous to those described above for methods of rapid detection of microorganisms. In an embodiment, the microorganism is a bacterium and the infectious agent is a bacteriophage. In a computerized system, the system may be fully automated, semi-automated, or directed by the user through a computer (or some combination thereof).

In some embodiments, the system may comprise a component for isolating the microorganism of interest from the other components in the sample.

In an embodiment, the invention comprises a system or kit comprising components for detecting a microorganism of interest comprising: a component for isolating at least one microorganism from other components in the sample; a component for infecting the at least one microorganism with a plurality of a parental infectious agent; a component for lysing the at least one infected microorganism to release progeny infectious agents present in the microorganism; and a component for detecting the progeny infectious agents, or with greater sensitivity, a soluble protein encoded and expressed by the infectious agent, wherein detection of the infectious agent or a soluble protein product of the infectious agent indicates that the microorganism is present in the sample. The infectious agent may comprise CBA120NanoLuc.

The systems or kits may comprise a variety of components for detection of progeny infectious agents. For example, in an embodiment, the progeny infectious agent (e.g., bacteriophage) may comprise an indicator moiety. In an embodiment, the indicator moiety in the progeny infectious agent (e.g., bacteriophage) may be a detectable moiety that is expressed during replication, such as a soluble luciferase protein.

In other embodiments, the invention may comprise a kit for rapid detection of a microorganism of interest in a sample, the system comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism in the sample. Such kits can include various embodiments and subembodiments analogous to those described above for methods of rapid detection of microorganisms. In an embodiment, the microorganism is a bacterium and the infectious agent is a bacteriophage.

In some embodiments, a kit may comprise a component for isolating the microorganism of interest from the other components in the sample.

These systems and kits of the invention include various components. As used herein, the term "component" is broadly defined and includes any suitable apparatus or collections of apparatuses suitable for carrying out the recited method. The components need not be integrally connected or situated with respect to each other in any particular way. The invention includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD or Blu-Ray drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims.

Accordingly, it is intended that the present invention not be limited to the described embodiments, but that it have the full scope defined by the language of the following claims, and equivalents thereof.

EXAMPLES

Results depicted in the following examples demonstrate detection of a low number of cells, even a single bacterium, in a shortened time to results.

Example 1. Creation of Indicator Phage from CBA120

Indicator Phage CBA120NanoLuc was created through homologous recombination using the following detailed procedures, as illustrated in FIGS. 1-3.

The genomic sequence of the CBA120 bacteriophage was available on the National Center for Biotechnology Information's GenBank, filed under "*Escherichia* phage Cba120," ID 12291. The genome was fully annotated, though most of the genes were labeled as "hypothetical protein," denoting that automated Open Reading Frame discover was used. Hypothetical proteins need only have a start and stop codon, and may not be expressed, as DNA regulation (promoters/enhancers/operators, etc.) are not defined in the sequence.

The late gene region was determined by comparison with other phage genomes. CBA120, and all other Vil-like phage, fall under the Vil-like phage group (genus Vil virus or Vi1 virus), which are related to T4-like phages. Bacteriophage T4 being the most studied bacteriophage, many of the genes homologs could be found, and were labeled as such. This includes the late gene region, which consists of the highly expressed phage structural proteins. This region was targeted for insertion of the NANOLUC® reporter gene. The major capsid protein was specifically identified. As the major capsid protein typically has the highest expression, inserting the reporter directly downstream of the major capsid protein can maximize expression of the reporter.

A sequence was designed to insert a codon-optimized NANOLUC® gene downstream of the major capsid protein. As illustrated in FIG. 2, a homologous recombination (HR) plasmid was designed, initially with 500 bp upstream and downstream of the insert point. Previous HR plasmids using Firefly Luciferase as a reporter gave poor transformation, which was alleviated by using a shorter downstream region. Presumably, there was a toxic effect with the full 500 bp region selected against in the bacteria. As such, the modified downstream region extends only about 300 bp.

The upstream region consisted of the 3' end of the major capsid protein, with the insert occurring immediately after the stop codon (TAA): SEQ ID NO: 1 ctttcatgctggaagttgaagcgaacggtatcggtgttgacacccgtcg tggtaaaggcaaccgtgttctgtgttctccgaacgtggcatccgctctg gcgatgtctggcatgctggactatgctccggttctgcaggaaaacacta aactggctgttgacccgactggccagaccttcgctggtgttctgtccaa cggtatgcgcgtctatgttgacccgtatgctgtagcagaatatatcacc ctggcatacaaaggcgcaactgcgctggatgccggtatcttcttcgcgc cgtatgtgccgctggaaatgtaccgcacccagggtgaaaccaccttcgc tccgcgtatggcgttcaaaacccgttacggcatctgtgctaacccgttc gtacagattccggctaaccaagacccgcaggtttacgtgactgctgacg gtattgctcaagacagcaacccgtatttccgcaaaggtctgatcaaatc tctgttctaa This was followed by an MluI restriction site, then a T4 late gene promoter consensus sequence, which consists of the -10 σ[70] factor consensus binding sequence (CTAAATAcCcc (SEQ ID NO: 2)). This promoter was designed based on compositing known -10 sequences. 14 random base pairs later, the ribosomal entry site, the Shine-Dalgarno consensus sequence (aaggaggt) was inserted, followed by 6 more random base pairs. The random base pairs were chosen to keep a similar GC content to other upstream untranslated regions. SEQ ID NO: 3 acgcgtCTAAATAcCccaaatactagtagataaggaggttttcga

A codon-optimized version of Promega's NANOLUC® with excretion signal, from pNL1.3 was inserted. SEQ ID NO: 4

ATGAATAGCTTTAGCACCAGCGCCTTTGGCCCTGTTGCCTTTAGCCTGGG

CCTGCTGCTGGTTCTGCCCGGCAGCATTTCCGGCCCCGGTGTTCACCCTGG

AAGATTTTGTGGGCGATTGGCGCCAGACCGCCGGTTATAACCTGGATCAG

GTGCTGGAACAGGGTGGTGTGAGCAGCCTGTTTCAGAATCTGGGCGTGAG

CGTGACCCCGATTCAGCGCATTGTGCTGAGCGGCGAGAACGGCCTGAAAA

TTGATATTCATGTTATTATTCCGTATGAGGGTCTGAGCGGCGATCAGATG

GGCCAGATTGAAAAAATCTTTAAGGTGGTGTATCCGGTGGACGACCATCA

TTTCAAGGTGATCCTGCATTACGGCACACTGGTGATTGACGGCGTTACCC

CGAACATGATCGACTATTTCGGCCGCCCGTATGAAGGTATCGCCGTGTTC

GACGGCAAGAAAATTACCGTGACCGGTACCCTGTGGAACGGCAACAAGAT

CATTGACGAGCGCCTGATTAACCCGGATGGTAGCCTGCTGTTTCGCGTGA

CCATTAATGGCGTGACCGGCTGGCGTCTGTGTGAACGCATCCTGGCCTAA

This was followed by 298 bp of the downstream HR segment, which includes a hypothetical gene. SEQ ID NO: 5 gcgacaggttttgataacaaacccgcttcggcggggttttctttatag ggatatgtaagataataaagcctcatttatcaaaggaggttaaaatgtct catcaattatctggcggtgcagtcgatactctattcgttcttttctggtt tggacctcgtgaagctggggaaatacctgctaaatctggagaagccgaat tggcctccctggggttttgtaaacgagttgatgttaaaaacgtaccaaaa ggtcgagatacacatctgtgtgtactcaccgaggaaggttacaaatac Following this, a consensus transcription terminator was inserted along with stop codons, which should only function on the plasmid to reduce any read through and possible toxic effects. As homologous recombination occurs only at the HR regions, the transcriptional terminator shouldn't be included in the recombinant phage. SEQ ID NO: 6

```
taaTTTGATAACAAACCCCGCTTCGGCGGGGTTTTCTTTATAGG
```

The full sequence was synthesized into a plasmid (GeneWiz). The plasmid was transformed into previously prepared E. coli O157:H7 electroporation competent cells using the protocol included in the Bio-Rad MicroPulser Electroporation Apparatus Operating Instructions and Applications Guide (catalog #165-2100).

Synthesized plasmid DNA (pUC57.CBA.HR.NanoLuc) (4 µg plasmid DNA) was dissolved in autoclaved filtered deionized water (40 µL) to make a 100 ng/µL stock. This plasmid (1 µL) was mixed with 20 µL thawed (on ice) E. coli O157:H7 electroporation competent cells (derived from non-toxic E. coli O157:H7 bacteria, ATCC 43888). The cell+DNA mix was transferred to an ice-cold Bio-Rad 0.1 cm electroporation cuvette, and subjected to the MicroPulser Electroporation Apparatus using program Ec1. The mix was immediately transferred into 1 mL Recovery Medium (Life Technologies), and incubated for 1 hour at 42° C., 220 rpm.

Aliquots of 1 µL, 100 µL, and the remainder of the culture concentrated by centrifugation (2 min @ 6800 g) and resuspended in 100 µL were plated onto selective medium (LB+Amp agar plates from Teknova) and incubated overnight at 37° C.

The next day, 23 colonies (+1 negative control) were screened by inoculating 100 µL LB+Amp and incubating for 2.5 hours at 37° C., then screened for luciferase activity. 5 µL of each culture were subjected to Promega NANO-GLO® luciferase assay, and read on a Promega GLOMAX® 96 luminometer. All 23 colonies were positive.

The top 3 wells were mixed and inoculated into 4 mL LB+Amp and grown to $1.8 \times 10^7$ cells/mL. Bacteria were infected with wild-type CBA120 bacteriophage from the Kutter lab (see Kutter et al., *Virology Journal* 2011, 8:430) at an MOI of 0.1, and the homologous recombination infection was incubated for 3 hours @ 37° C.

Bacterial concentration was monitored for 4 hours; bacteria doubled by 2 hours, then began to drop, indicating a successful phage infection.

Example 2. Isolation of CBA120NanoLuc

Following homologous recombination to generate recombinant bacteriophage genomes, a series of titer and enrichment steps was used to isolate a specific recombinant bacteriophage that expresses NANOLUC®.

To reduce background NANOLUC® signal from plasmid expression, the lysate was washed 3 times with TMS in an Amicon Ultra Concentrator, spun to concentrate the volume from 4 mL to 500 µL; TMS was added to bring the volume to 4 mL, and this series was repeated.

In order to determine the initial ratio of recombinant to wild-type phage, limiting dilution assays based on the TCID50 (tissue culture infectious dose 50%) were used to both determine the concentration of infectious units (IU/mL), akin to number of virus particles or plaque forming units, and to determine the number of luciferase transducing units (TU/mL). In these assays, the sample was serially diluted, with each dilution aliquoted into replicate wells with E. coli O157:H7 bacteria. Any wells that showed luciferase activity must have been infected with at least one recombinant phage. Any wells that showed cell lysis had been infected by at least one phage. Based on the highest dilution where each of these cases occurred, the original concentrations were back-calculated. These initial phage mixtures from transformed cells typically yielded a ratio of 20,000 wild-type IU for each recombinant phage TU. Steps were then taken to isolate and amplify the recombinant phage.

As illustrated in FIG. 4, in some experiments recombinant phage were isolated from a mixture comprising 0.83% of total phage. The phage mixtures were diluted into 96 well plates to give an average of 3 recombinant TU per plate, which corresponds to about 3.8 infectious units (IU) of mostly wild-type phage per well. Bacteria were added such that each well contained 50 µL of turbid E. coli O157:H7. After 2 hours of incubation at 37° C., wells were sampled and screened for the presence of luciferase. Any positive wells are likely to have been inoculated with a single recombinant phage, and at this stage the mixture contained an enriched ratio of 1 recombinant phage: 3.8 wild-type phage, which is an enrichment over the original 1:120 ratio. Of 96 wells screened, 7 were positive. Further rounds of limiting dilution assay were not necessary in this experiment.

A plaque assay was performed, wherein plaques were individually picked and screened for luciferase transducing ability, insuring about 3 recombinants were in the mix of plaques being screened. Each plaque was suspended in 100 µL TMS, and 5 µL was added to a well containing a turbid E. coli O157:H7 culture, and wells were assayed after incubation for 45 minutes to 1 hour at 37° C.

Positive wells were expected to contain a pure culture of recombinant phage, but an additional round of plaque purification was performed. Finally, large-scale production was performed to obtain high titer stocks appropriate for use in the E. coli O157:H7 detection assay. Cesium chloride isopycnic density gradient centrifugation was used to separate phage particles from contaminating luciferase protein to reduce background.

Example 3. Bacterial Detection Using CBA120NanoLuc Indicator Phage

Detection of E. coli O157:H7 using the CBA120NanoLuc Indicator Phage was tested in experiments using the basic assay format depicted in FIG. 6. First, cell numbers ranging from 1-10,000 were taken from cultures and infected with $10^5$, $10^6$, and $10^7$ phage/mL in identical sample volumes of LB for 2 hours. Following the addition of lysis buffer and NANO-GLO® reagent, the reaction was read using a GLOMAX® 96 instrument. FIG. 7 shows that the highest ratio of signal/background was achieved with $10^6$ phage/mL used for infecting the sample.

FIG. 8 shows the data from 6-10 replicates, each using the same cell numbers from cell cultures in LB. A phage concentration of $10^6$ phage/mL was used for infecting the sample, and infected cells were incubated for 2 hours at 37° C. Following the addition of lysis buffer and NANO-GLO® reagent, the reaction was read using a GLOMAX® 96 instrument. FIG. 8 shows that CBA120NanoLuc can detect a single (1) cell with a signal that is significantly higher than background.

FIG. 9 shows from the data of FIG. 8 that CBA120NanoLuc can detect a single (1) E. coli O157:H7 cell with a signal to background ratio of >2.0.

The performance of CBA120NanoLuc indicator phage for detecting E. coli O157:H7 was also certified Aug. 1, 2016 by the AOAC Research Institute (Certificate No. 081601).

Example 4. Bacterial Detection in Beef Assays Using CBA120NanoLuc

CBA120NanoLuc was used to detect E. coli O157:H7 in beef assays. For all of the beef experiments, 50 RLU was used as the background value, and 3 times background value was considered positive (i.e., >150 RLU is positive, or Signal/Background >3.0). There were no false positives or negatives when compared to the secondary confirmation method described below.

For 25 g beef samples, pre-warmed TSB medium (42° C.) was added to the sample to 1:3 sample:medium (25 g:75 mL). The sample was blended with a Stomacher for 30 seconds on low setting/or equivalent, followed by incubation at 42° C. without shaking. The bag was closed by folding over the top 2-3 times and clipping closed. After 5 hours (for 10 mL aliquots in the next step) or 6 hours (for 1 mL aliquots in the next step) of enrichment at 42° C., the bag was gently massaged to thoroughly mix the contents.

An aliquot of either 1 mL or 10 mL was removed from the bag for testing. These correspond to the "1 mL concentration" or "10 mL concentration" in the data presented for all beef assay experiments in FIGS. 10-16.

Aliquots of 10 mL were centrifuged at 3400 g for 5 minutes, the supernatant was discarded, and the contents were resuspended in 1 mL pre-warmed TSB. The CBA120 Indicator Phage was added to infect any target bacteria in the sample by adding 10 µL of $1\times10^8$ phage/mL.

Aliquots of 1 mL were centrifuged for 1 minute at the highest speed in a microfuge, the supernatant was discarded, and the contents were resuspended in 200 µL pre-warmed TSB. To infect target bacteria, 15 µL of $1.2\times10^7$ phage/mL of the CBA120 Indicator Phage was added.

Samples with CBA120 Indicator Phage were incubated for 2 hours at 37° C., vortexed briefly, centrifuged for 5-10 seconds to pellet debris, and 150 µL sample was transferred to a 96-well plate (being careful not to disturb debris pellet). Lysis buffer (10 µL) was added to each well and gently mixed by pipetting. Freshly prepared NANO-GLO® reagent (50 µL) was added to each well and gently mixed by pipetting (or automatically injected). (NANO-GLO® reagent was prepared diluting the NANO-GLO® Luciferase Assay Substrate 1:50 into NANO-GLO® Luciferase Assay Buffer, e.g., to make 1 mL of NANO-GLO® reagent, and 20 µL of NANO-GLO® Luciferase Assay Substrate was added to 1 mL of NANO-GLO® Luciferase Assay Buffer.)

The plate was read on a GLOMAX® 96 instrument 3 minutes after substrate addition.

Secondary Confirmation Method:

Confirmation of E. coli O157:H7 was performed on overnight-enriched cultures using immuno-magnetic separation (IMS) with particles coated with O157 antibodies (DYNABEADS®, Life Technologies #71004) and plating onto selective plates (CHROMAGAR® plates, BD #214984).

To prepare for the confirmation, the samples were incubated overnight (18-24 hours total or 13-19 additional hours) at 42° C.±1°. From the overnight culture, 1 mL was removed and the DYNABEADS® anti-E. coli O157 procedure was followed. Briefly, 20 µL of IMS particles were added to the diluted overnight culture and incubated for 10 minutes at room temperature. Magnetic particles were isolated for 3 minutes with the magnet, then washed 3 times with PBS, 1 ml per wash. After the final wash, particles were plated onto CHROMAGAR® plates (BD #214984) and incubated 18-24 hours at 37° C.±1°.

Mauve-colored colonies (presumptive positive) were cultured in TSB media overnight (18-24 hours) at 37° C.±1° for serological confirmation. Presence of O157 and H7 antigens was determined using an agglutination assay (Remel Wellcolex E. coli O157:H7 #R30959601). The manufacturer's instructions were followed, using 40 µL of the overnight culture. Results confirmed presence or absence of O157 and/or H7 antigens and provided confirmation for E. coli O157:H7.

Data from 25 g beef samples are shown in FIGS. 10-12. FIGS. 10-11 correspond to the 1 mL concentration and FIG. 12 to the 10 mL concentration of enriched samples. All positives were detected after 6 hours enrichment for the 1 mL concentration and after 5 hours enrichment for the 10 mL concentration. FIGS. 11-12 show confirmation by DYNABEADS®/CHROMAGAR® plating.

For larger (125 g) beef samples, experiments were performed with both ground beef and beef trim. The procedure was similar, except that beef trim samples required treatment with the stomacher for at least 120 seconds on high setting/or equivalent. Enrichment for either sample type followed for 8 hours at 42° C., and the rest of the procedure was as described above.

Data from 125 g beef samples are shown in FIGS. 13-16. FIGS. 13 and 15 correspond to the 1 mL concentration and FIGS. 14 and 16 correspond to the 10 mL concentration. FIGS. 15-16 show confirmation by DYNABEADS®/CHROMAGAR® plating. All positives were detected after 7 hours of enrichment.

Example 5. Vegetable Wash Assays

Data from spinach wash filter assays are shown in FIG. 17, which shows that the assay can detect 1 cell of E. coli O157:H7 in 100 mL of spinach wash following 3 hours of enrichment. These results were confirmed by using the DYNABEADS®/CHROMAGAR® tests on overnight cultures of each sample according to the manufacturer's instructions, as described in the "Secondary Confirmation Method" above.

To prepare the vegetable wash, vegetable leaves (e.g., spinach or lettuce) were weighed and added to a clean plastic bag. Five mL of water was added per each gram (g) of vegetable. Leaves and solution were mixed manually for a few minutes. Liquid was then extracted from the plastic bag and used as the "vegetable wash." Using this method, ~1 million bacteria were found by CFU to reside on a single spinach leaf (1-2 g).

Next, 100 mL of "vegetable wash" was vacuum filtered through a 47 mm 0.45 µM filter. The filter was removed and placed in a small sealable plastic bag. Prewarmed (42° C.) TSB medium (600 µL) was added to the bag to cover the filter. The filter was then incubated at 42° C. for 3 hours with gentle agitation. An aliquot of enriched media (300 µL) was removed for confirmation purposes. CBA120NanoLuc Indicator Bacteriophage was then added to the remaining medium in the bag to a final concentration of $1\times10^6$ phage/mL, and the bag was agitated gently followed by incubation for 2 hours at 37° C. Finally, 100-150 µL of the infection reaction was transferred to a 96-well plate. Lysis buffer (10 µL) and prepared NANO-GLO® reagent (50 µL) were added and the sample was read on a luminometer (GLOMAX® 96).

FIG. 17 shows data from a spinach wash assay, including confirmatory results from DYNABEADS®/CHROMAGAR® plating. The ability to discern a single target bacterial cell from $10^5$ non-target bacteria in vegetable wash is surprising and again demonstrates the specificity and sensitivity of the assay.

We claim:

1. A recombinant bacteriophage comprising an indicator gene inserted into a late gene region of the bacteriophage CBA120 genome, wherein the indicator gene is not contiguous with a gene encoding a structural bacteriophage protein and does not yield a fusion protein, and wherein expression of the indicator gene results in an indicator protein product.

2. The recombinant bacteriophage of claim 1, wherein the recombinant bacteriophage specifically infects *E. coli* O157:H7.

3. The recombinant bacteriophage of claim 1, wherein the indicator gene is codon-optimized and encodes a soluble protein product that generates an intrinsic signal or a soluble enzyme that generates signal upon reaction with substrate.

4. The recombinant bacteriophage of claim 3, further comprising an untranslated region upstream of the codon-optimized indicator gene, wherein the untranslated region includes a bacteriophage late gene promoter and a ribosomal entry site.

5. A method of preparing a recombinant indicator bacteriophage comprising:
   selecting a wild-type bacteriophage that specifically infects a target pathogenic bacterium, wherein the wild-type bacteriophage is CBA120 and the target pathogenic bacterium is *E. coli* O157:H7;
   preparing a homologous recombination plasmid/vector comprising an indicator gene, wherein preparing a homologous recombination plasmid/vector comprises:
   determining the natural nucleotide sequence in the late region of the genome of the selected bacteriophage;
   annotating the genome and identifying the major capsid protein gene of the selected bacteriophage;
   designing a sequence for homologous recombination downstream of the major capsid protein gene, wherein the sequence comprises a codon-optimized indicator gene;
   and
   incorporating the sequence designed for homologous recombination into a plasmid/vector;
   transforming the homologous recombination plasmid/vector into target pathogenic bacteria;
   infecting the transformed target pathogenic bacteria with the selected wild-type bacteriophage, thereby allowing homologous recombination to occur between the plasmid/vector and the bacteriophage genome; and
   isolating a particular clone of recombinant bacteriophage.

6. The method of claim 5, wherein designing a sequence further comprises inserting an untranslated region including a phage late gene promoter and ribosomal entry site upstream of the codon-optimized indicator gene.

7. The method of claim 5, wherein the homologous recombination plasmid comprises an untranslated region including a bacteriophage late gene promoter and a ribosomal entry site upstream of the codon-optimized indicator gene.

8. The method of claim 5, wherein isolating a particular clone of recombinant bacteriophage comprises a limiting dilution assay for isolating a clone that demonstrates expression of the indicator gene.

9. A method for detecting *E. coli* O157:H7 in a sample comprising:
   incubating the sample with a recombinant CBA120 bacteriophage, wherein the recombinant bacteriophage comprises an indicator gene inserted into the late gene region of the bacteriophage genome, wherein the indicator gene is not contiguous with a gene encoding a structural bacteriophage protein and does not yield a fusion protein, and wherein expression of the indicator gene results in an indicator protein product; and
   detecting the indicator protein product, wherein positive detection of the indicator protein product indicates that *E. coli* O157:H7 is present in the sample.

10. The method of claim 9, wherein the sample is a food, environmental, water, commercial, or clinical sample.

11. The method of claim 9, wherein the method detects as few as 10, 9, 8, 7, 6, 5, 4, 3, 2, or a single bacterium in a sample of a standard size for the food safety industry.

12. The method of claim 10, wherein the sample comprises beef or vegetables.

13. The method of claim 9, wherein the sample is first incubated in conditions favoring growth for an enrichment period of 9 hours or less, 8 hours or less, 7 hours or less, 6 hours or less, 5 hours or less, 4 hours or less, 3 hours or less, or 2 hours or less.

14. The method of claim 9, wherein the total time to results is less than 12 hours, less than 11 hours, less than 10 hours, less than 9 hours, less than 8 hours, less than 7 hours, or less than 6 hours.

15. A kit for detecting *E. coli* O157:H7 comprising a recombinant bacteriophage derived from CBA120, wherein the recombinant bacteriophage comprises an indicator gene inserted into the late gene region of the bacteriophage genome, wherein the indicator gene is not contiguous with a gene encoding a structural bacteriophage protein and does not yield a fusion protein, and wherein expression of the indicator gene results in an indicator protein product.

16. The kit of claim 15, further comprising a substrate for reacting with an indicator to detect the soluble protein product expressed by the recombinant bacteriophage.

17. A system for detecting *E. coli* O157:H7 comprising a recombinant bacteriophage derived from CBA120, wherein the recombinant bacteriophage comprises an indicator gene inserted into the late gene region of the bacteriophage genome, wherein the indicator gene is not contiguous with a gene encoding a structural bacteriophage protein and does not yield a fusion protein, and wherein expression of the indicator gene results in an indicator protein product.

18. The method of claim 9, wherein prior to incubating with the sample, the recombinant CBA120 bacteriophage is purified to remove any residual indicator protein product generated during production, such that the recombinant CBA120 bacteriophage is substantially free of indicator protein product.

* * * * *